(12) United States Patent
Konofagou et al.

(10) Patent No.: US 11,678,859 B2
(45) Date of Patent: Jun. 20, 2023

(54) SYSTEMS AND METHODS FOR RENDERING OF CARDIAC ELECTROMECHANICAL ACTIVATION

(71) Applicant: THE TRUSTEES OF COLUMBIA UNIVERSITY IN THE CITY OF NEW YORK, New York, NY (US)

(72) Inventors: Elisa Konofagou, New York, NY (US); Pierre Nauleau, New York, NY (US); Elaine Wan, Fresh Meadows, NY (US); Lea Melki, New York, NY (US); Julien Grondin, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/572,328

(22) Filed: Sep. 16, 2019

(65) Prior Publication Data

US 2020/0214662 A1    Jul. 9, 2020

Related U.S. Application Data

(63) Continuation of application No. PCT/US2018/022950, filed on Mar. 16, 2018.
(Continued)

(51) Int. Cl.
*A61B 8/08* (2006.01)
*A61B 8/00* (2006.01)

(52) U.S. Cl.
CPC .......... *A61B 8/0883* (2013.01); *A61B 8/4416* (2013.01); *A61B 8/4488* (2013.01);
(Continued)

(58) Field of Classification Search
CPC ... A61B 8/0883; A61B 8/4416; A61B 8/4488; A61B 8/485; A61B 8/5223;
(Continued)

(56) References Cited

U.S. PATENT DOCUMENTS

| 2003/0236466 A1 | 12/2003 | Tarjan et al. |
| 2004/0002652 A1* | 1/2004 | Phelps ............. G01S 7/5202 600/437 |

(Continued)

OTHER PUBLICATIONS

Alexandre Costet, Jean Provost, Alok Gambhir, Yevgeniy Bobkov, Peter Danilo, Gerard J.J. Boink, Michael R. Rosen, Elisa E. Konofagou, Electromechanical Wave Imaging of Biologically and Electrically Paced Canine Hearts in Vivo, Ultrasound in Medicine & Biology, vol. 40, Issue 1, 2014 (Year: 2014).*

(Continued)

*Primary Examiner* — Patricia J Park
(74) *Attorney, Agent, or Firm* — Baker Bottts L.L.P.

(57) ABSTRACT

Systems and methods for generating an electromechanical map are disclosed herein. The methods includes obtaining ultrasound data comprising a series of consecutive image frames and radio frequency (RF) signals corresponding to the location in the heart; measuring displacements and strains based on the ultrasound data to determine an electromechanical activation in the location; converting the ultrasound data into a series of isochrone maps; and combining the series of isochrone maps to generate the electromechanical map. The electromechanical map illustrates the electromechanical activation and internal wall structures of the heart.

17 Claims, 35 Drawing Sheets
(33 of 35 Drawing Sheet(s) Filed in Color)

Related U.S. Application Data

(60) Provisional application No. 62/474,834, filed on Mar. 22, 2017, provisional application No. 62/473,124, filed on Mar. 17, 2017.

(52) U.S. Cl.
CPC ............ *A61B 8/485* (2013.01); *A61B 8/5223* (2013.01); *A61B 8/5261* (2013.01); *A61B 2576/023* (2013.01)

(58) Field of Classification Search
CPC . A61B 8/5261; A61B 2576/023; A61B 5/339; A61B 5/7289; A61B 5/11; G16H 30/40
See application file for complete search history.

(56) References Cited

U.S. PATENT DOCUMENTS

| | | | |
|---|---|---|---|
| 2005/0154310 A1 | 7/2005 | Bruestle | |
| 2015/0289840 A1* | 10/2015 | Konofagou | A61B 8/463 600/438 |
| 2015/0320331 A1* | 11/2015 | van Dam | A61B 5/349 600/411 |
| 2016/0249880 A1 | 9/2016 | Konofagou et al. | |
| 2017/0011197 A1* | 1/2017 | van Dam | G06T 19/20 |

OTHER PUBLICATIONS

Costet et al., "Electromechanical wave imaging (EWI) validation in all four cardiac chambers with 3D electroanatomic mapping in canines in vivo," Phys. Med. Biol. 61:8105-8119 (2016).

International Search Report dated Jun. 6, 2018 in International Application No. PCT/US2018/022950.

Konofagou et al., "Electromechanical wave imaging for noninvasive mapping of the 3D electrical activation sequence in canines and humans in vivo," J Biomech. 45(5):856-864 (2012).

Seo et al., "Left ventricular activation imaging by 3-dimensional speckle-tracking echocardiography. Comparison with electrical activation mapping," Circ J. 77(10):2481-2489 (2013).

* cited by examiner

FIG. 5A
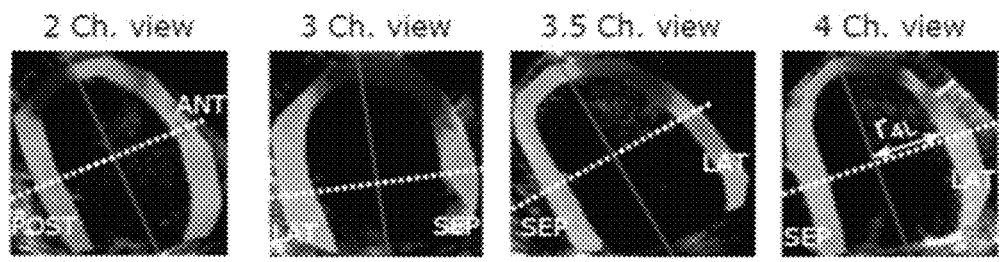
FIG. 5B
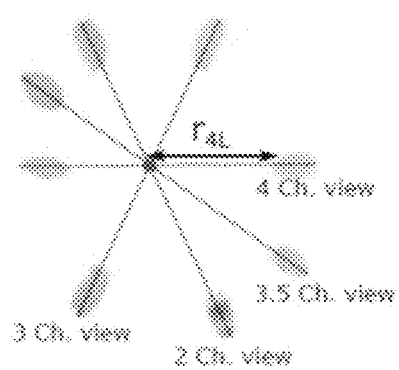
FIG. 5C
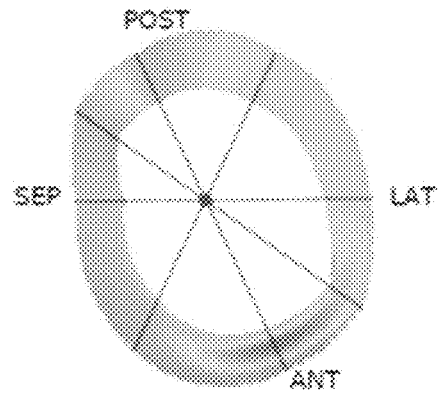
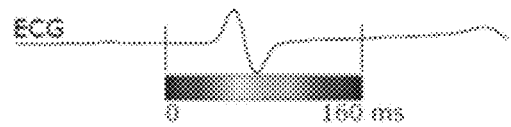

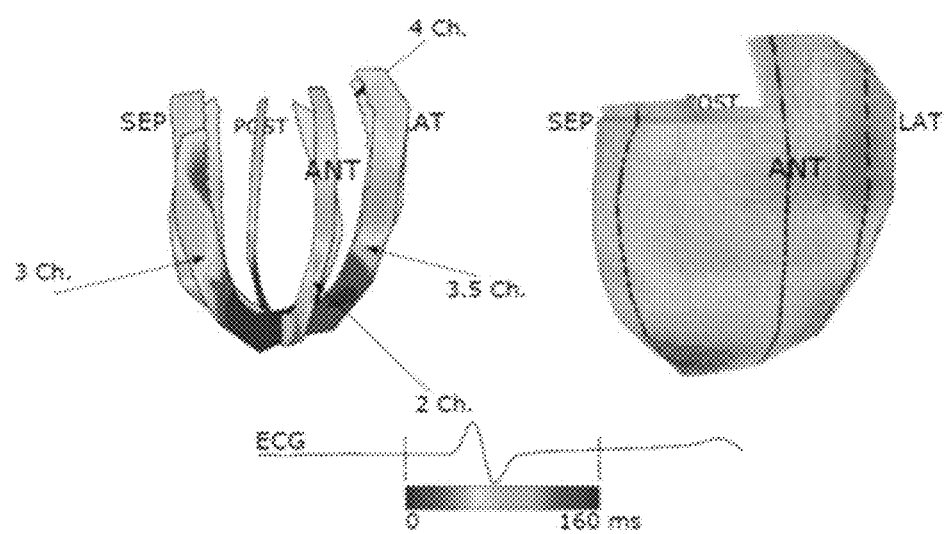

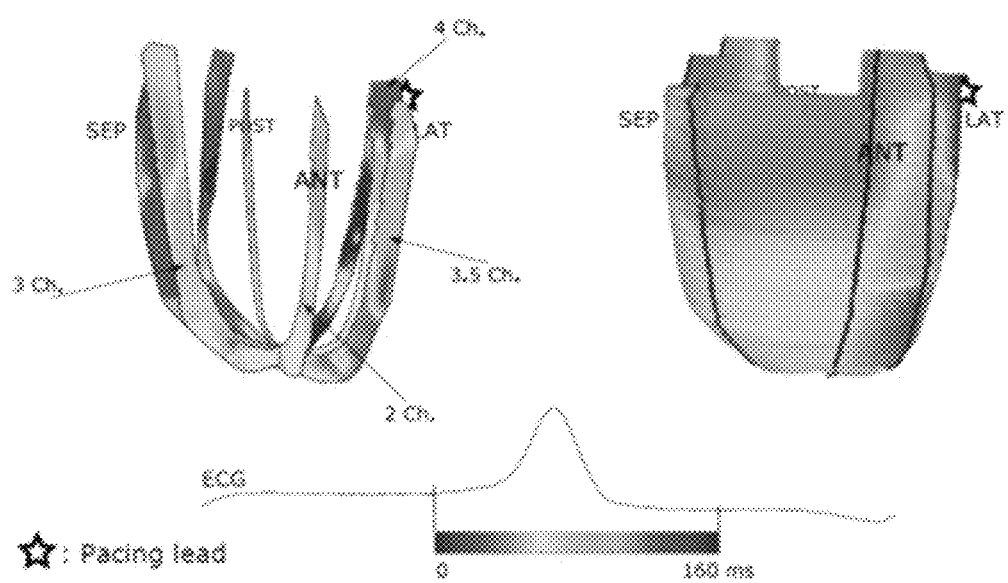

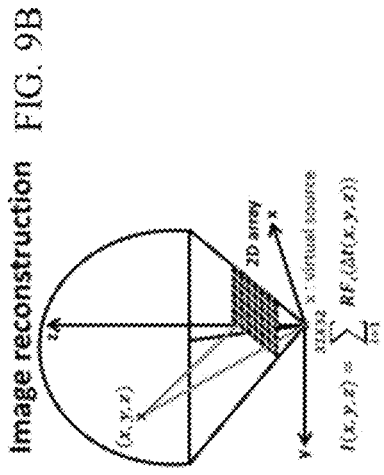
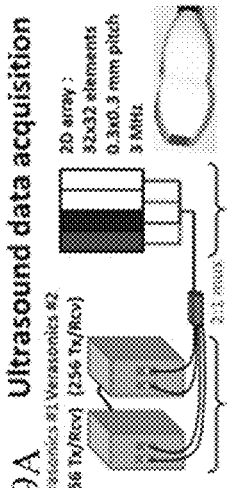
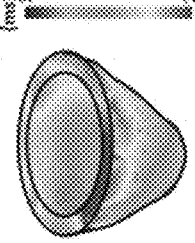
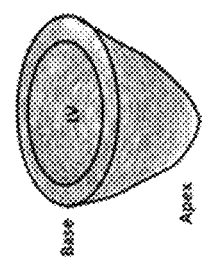
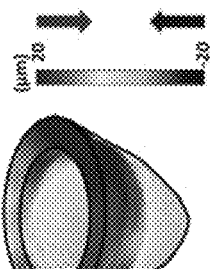
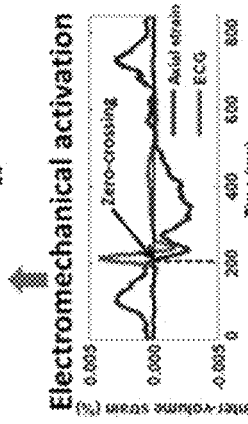
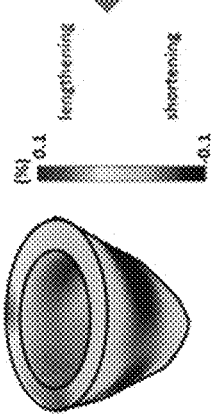
FIG. 9A Ultrasound data acquisition
FIG. 9B Image reconstruction
FIG. 9C Image segmentation
FIG. 9D Inter-volume displacement
FIG. 9E Inter-volume strain
FIG. 9F Electromechanical activation
FIG. 9G Activation map Simulated EWI of a normal human heart Simulated EWI of an infarcted human heart FIG. 11A  
t = 52 ms
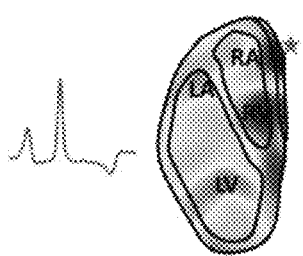
FIG. 11B  
t = 122 ms
FIG. 11C  
t = 172 ms
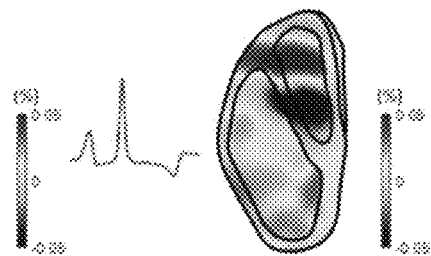
FIG. 11D  
t = 192 ms
FIG. 11E  
t = 292 ms
FIG. 11F  
isochrone
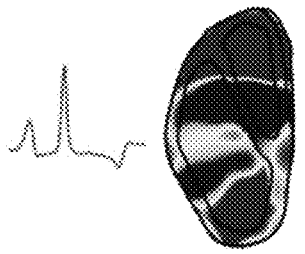
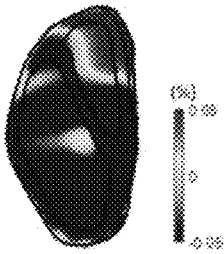
EWI of a canine during normal sinus rhythm

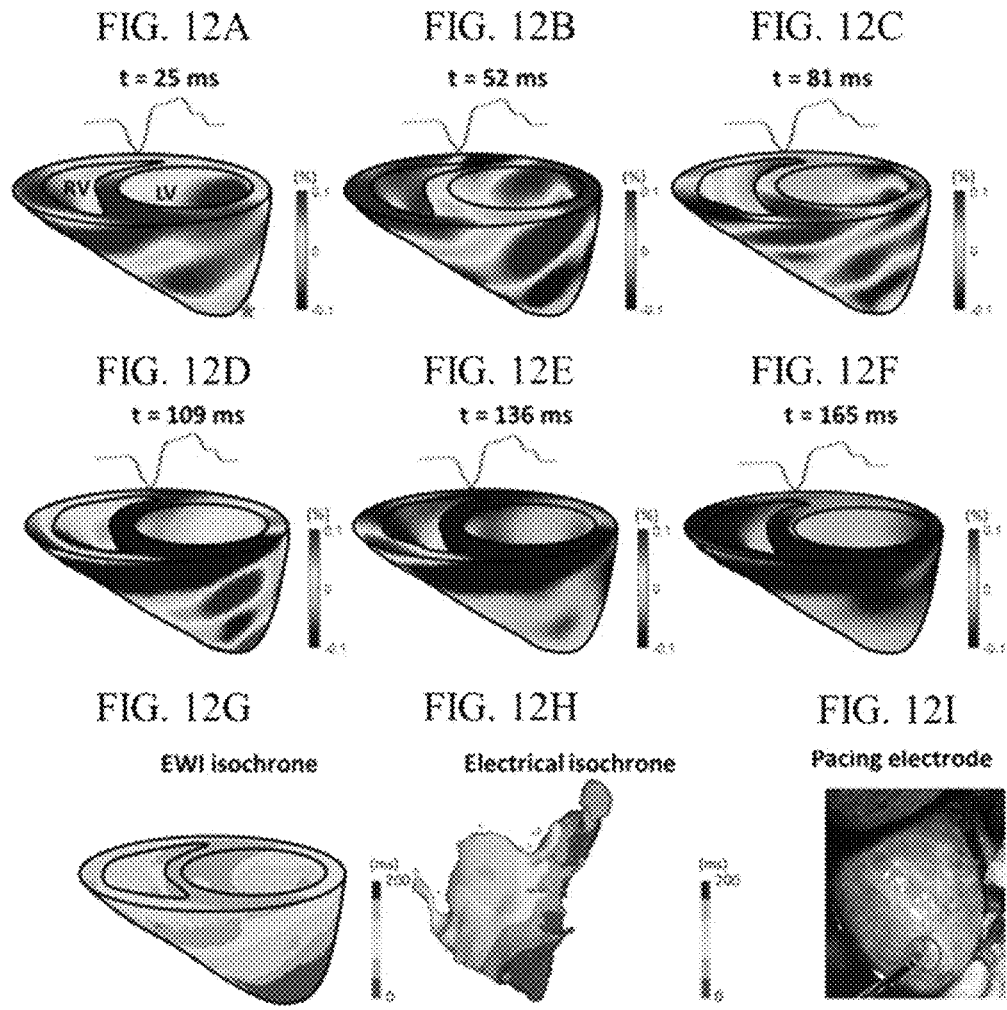
EWI of a canine during apical pacing t = 42 ms t = 88 ms t = 134 ms t = 180 ms EWI isochrone Pacing electrode EWI of a canine during lateral LV pacing t = 10 ms t = 35 ms t = 60 ms t = 85 ms t = 110 ms EWI isochrone EWI of a human during normal sinus rhythm

WPW: left lateral AP

PVC : left anterior papillary muscle

FIG. 17A
FIG. 17B
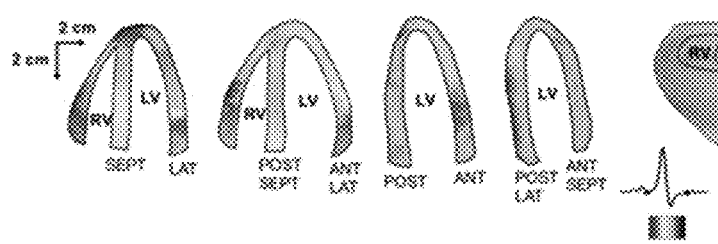
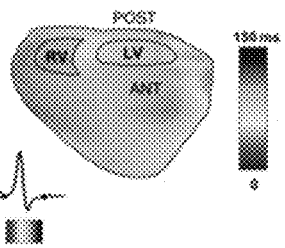
FIG. 17C  FIG. 17D
FIG. 17E
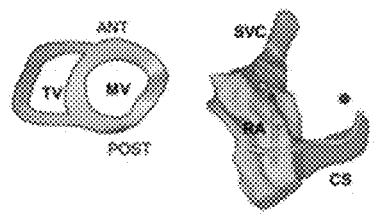
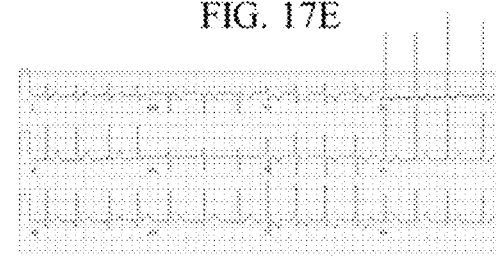
FIG. 17F
FIG. 17G
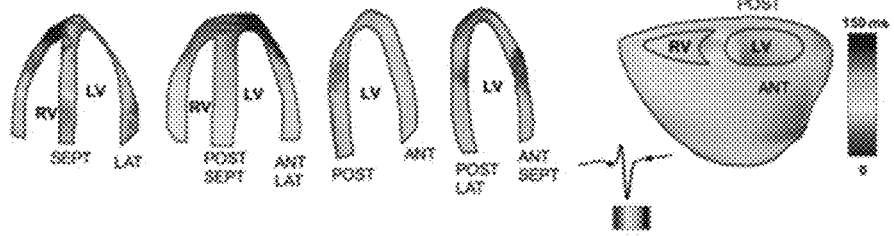
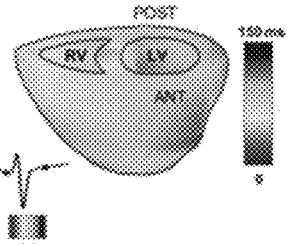
FIG. 17H
FIG. 17I
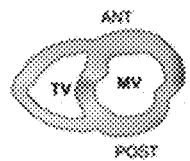

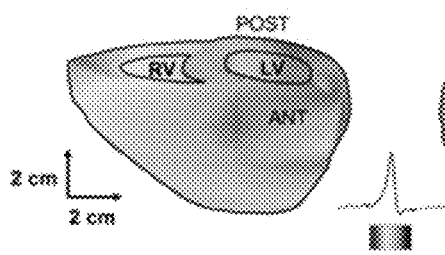
FIG. 18A   FIG. 18B   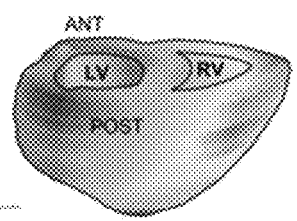 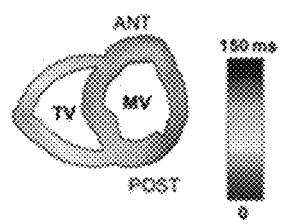
FIG. 18C
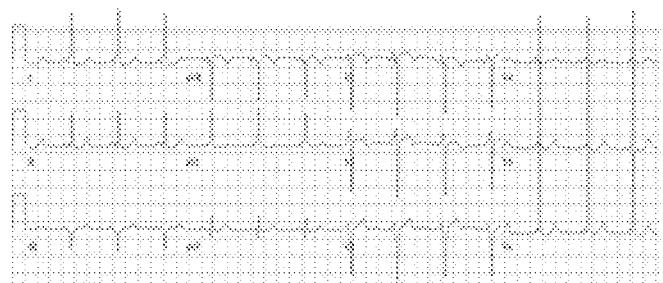
FIG. 18E
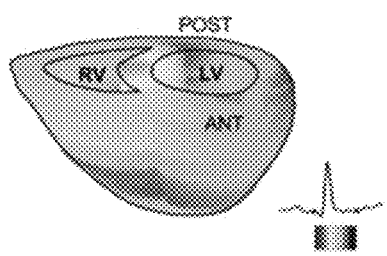 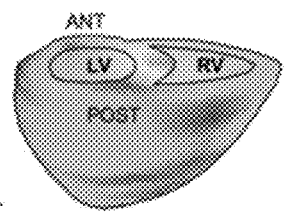 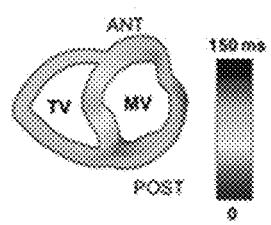
FIG. 18F   FIG. 18G   FIG. 18H FIG. 19A    FIG. 19B    FIG. 19C
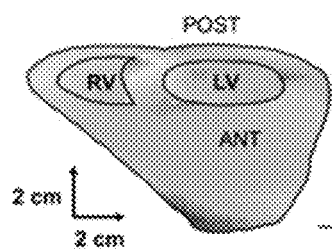 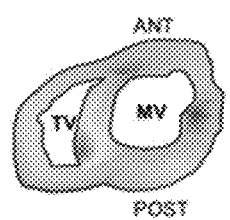 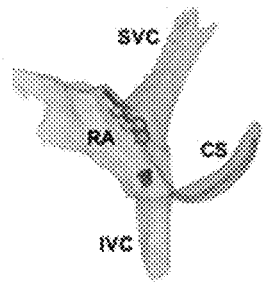
FIG. 19D

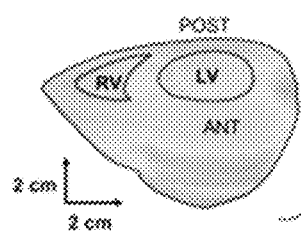 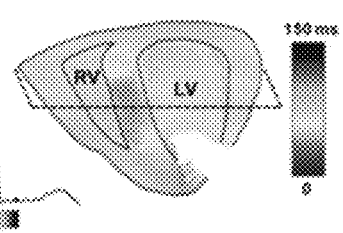 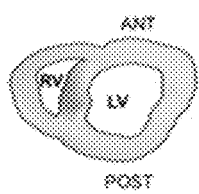
FIG. 20A  FIG. 20B  FIG. 20C
FIG. 20D
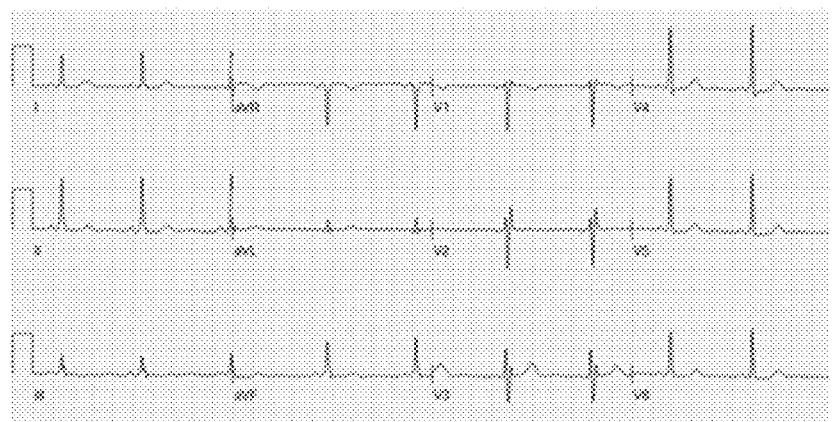

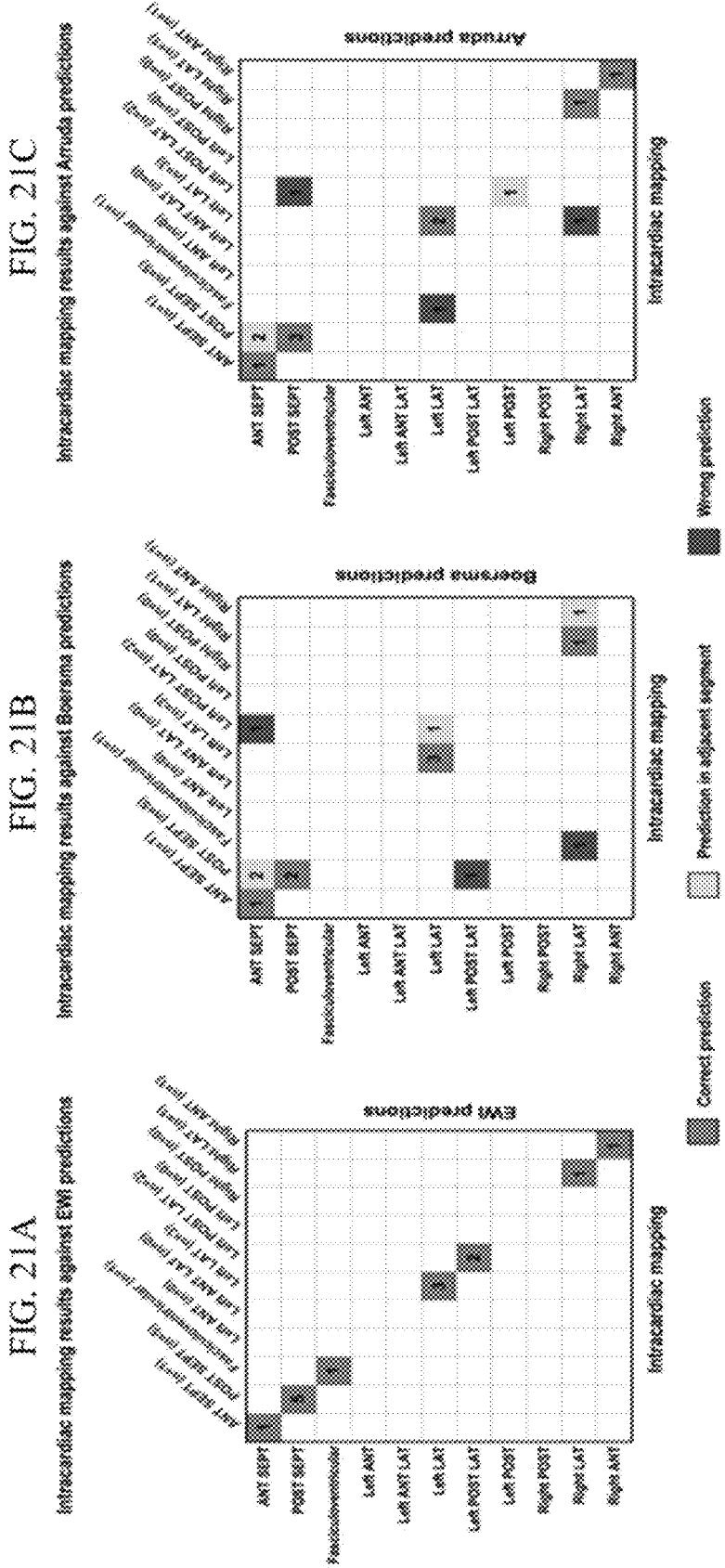

FIG. 23A
Wolff-Parkinson-White syndrome
FIG. 23B
Premature Ventricular Contraction
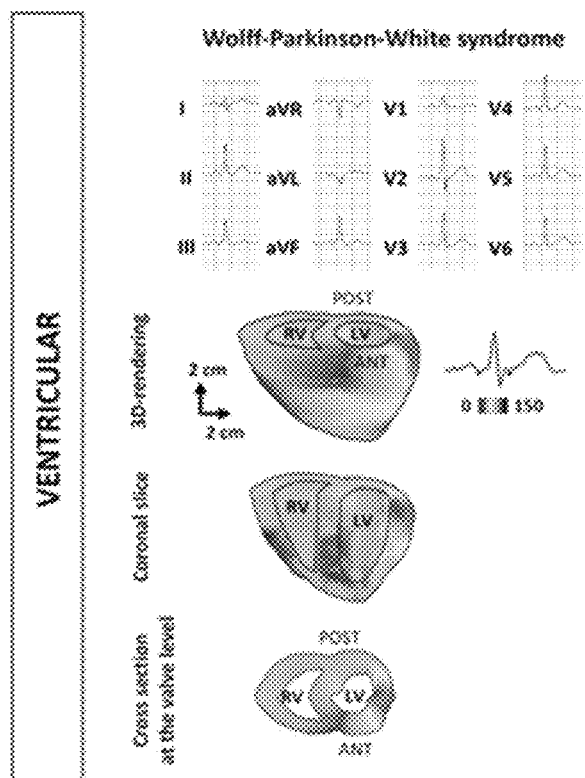
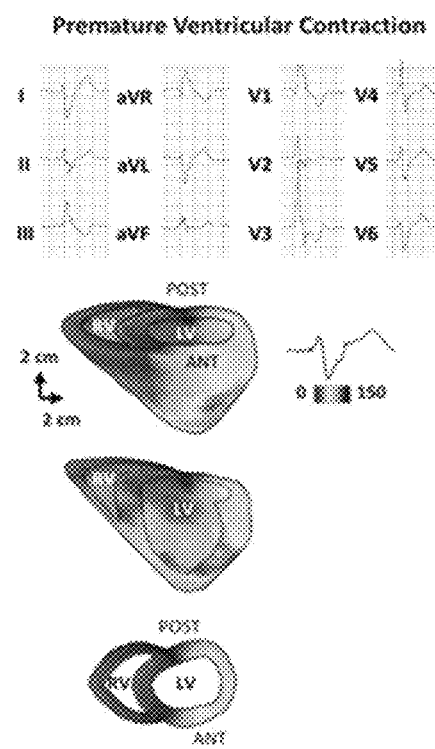
FIG. 23C
Atrial Tachycardia
FIG. 23D
Atrial Flutter
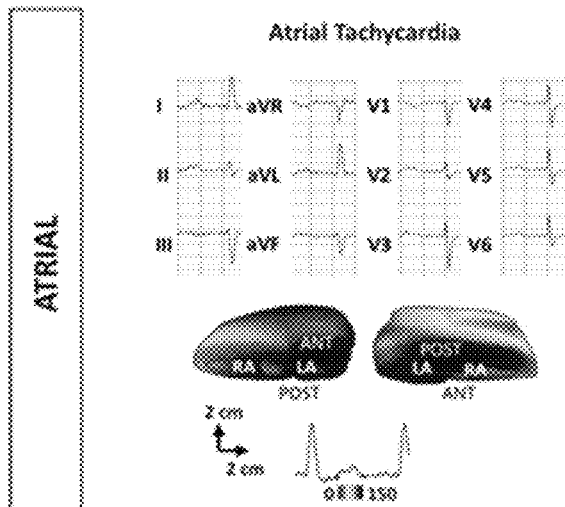
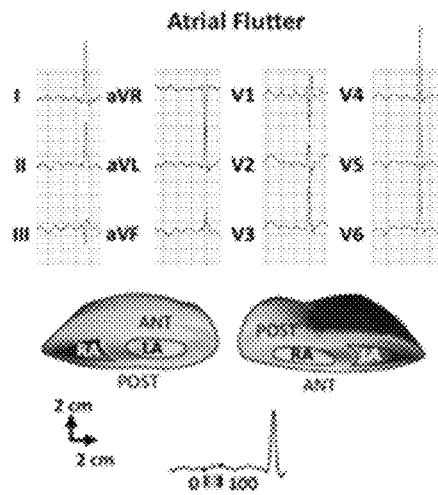

FIG. 25A
FIG. 25B
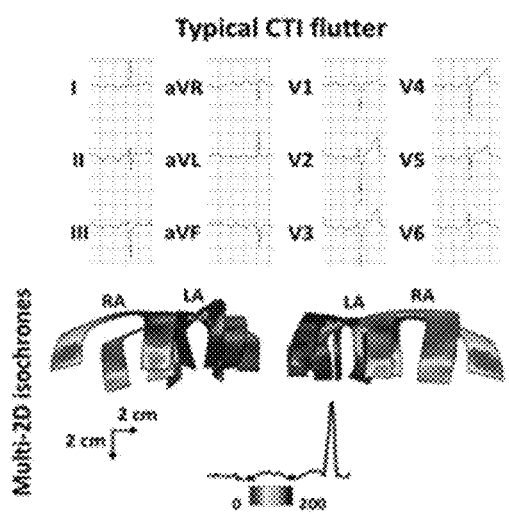
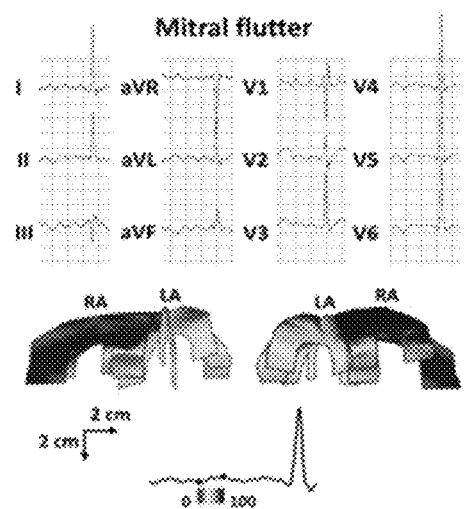

FIG. 28

VENTRICULAR SEGMENTS

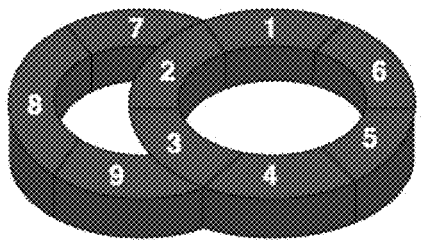

BASAL
1. Posterior
2. Posteroseptal
3. Anteroseptal
4. Anterior
5. Anterolateral 6. Posterolateral
7. RV Posterior
8. RV Free Wall
9. RV Anterior

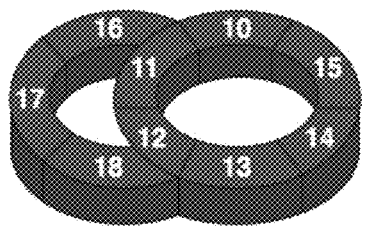

MID
10. Posterior
11. Posteroseptal
12. Anteroseptal
13. Anterior
14. Anterolateral 15. Posterolateral
16. RV Posterior
17. RV Free Wall
18. RV Anterior

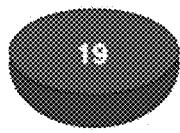

19. Apex

20. RVOT
21. LVOT

ATRIAL CLASSIFICATION CATEGORIES

I. Typical right sided CTI associated
II. Other right sided
III. Left sided

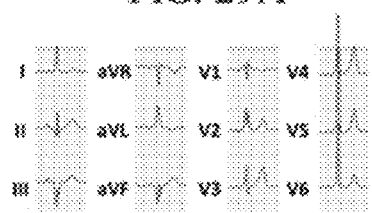
FIG. 29A
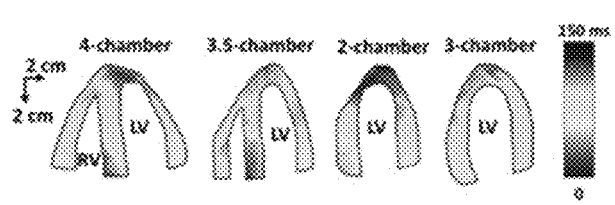
FIG. 29B
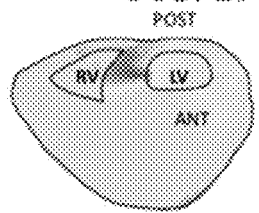
FIG. 29C
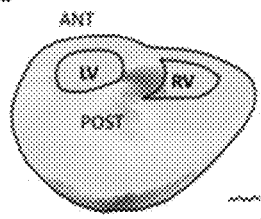
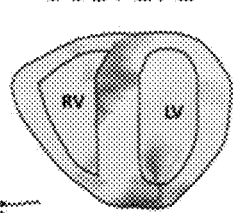
FIG. 29D
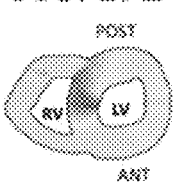
FIG. 29E FIG. 30A
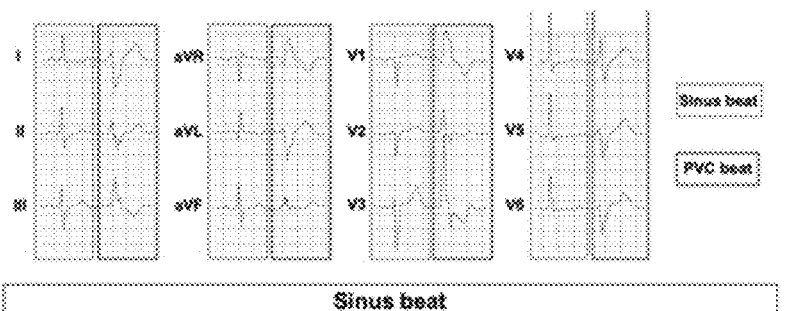
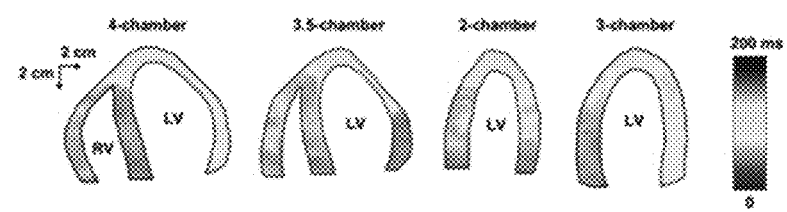
FIG. 30B
FIG. 30C  FIG. 30D
FIG. 30E
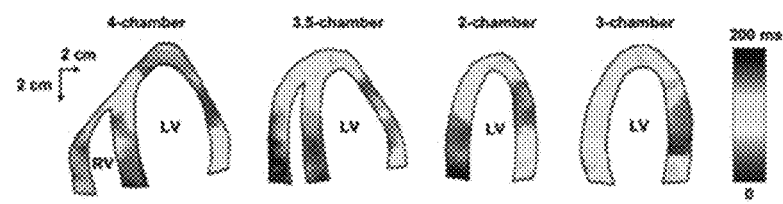
FIG. 30F  FIG. 30G FIG. 34A
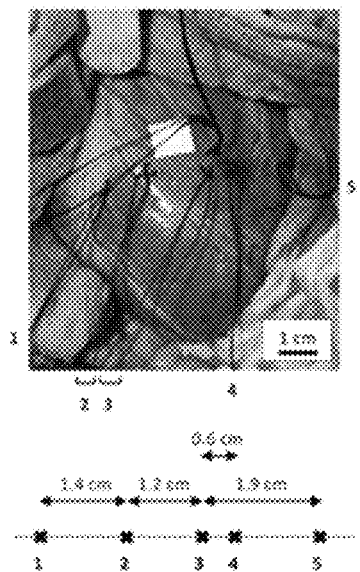
FIG. 34B
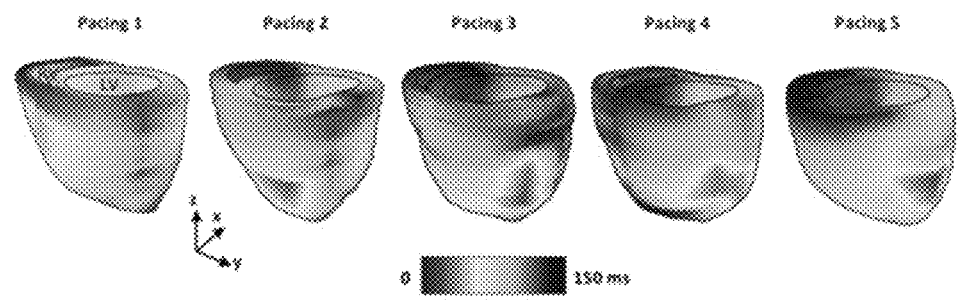
FIG. 34C

SYSTEMS AND METHODS FOR RENDERING OF CARDIAC ELECTROMECHANICAL ACTIVATION

CROSS-REFERENCE TO RELATED APPLICATIONS

This application is a continuation-in-part of International Patent Application No. PCT/US18/022950, filed on Mar. 16, 2018, which claims priority to U.S. Provisional Patent Application Ser. No. 62/473,124, filed Mar. 17, 2017, and U.S. Provisional Patent Application Ser. No. 62/474,834, filed on Mar. 22, 2017, each of which is hereby incorporated by reference in their entirety and from which priority is claimed.

GOVERNMENT SUPPORT

This invention was made with government support under Grant Nos. R01-HL114358, R01-HL140646-01, R01-EB006042, and R01-HL114358 awarded by the National Institutes of Health (NIH). The government has certain rights in the invention.

BACKGROUND

Arrhythmia is a type of heart disease involving abnormal electromechanical activation of the heart wall. Certain cardiac arrhythmias, such as atrial fibrillation and ventricular tachycardia, can be associated with certain causes of death, such as stroke and cardiac sudden arrest. The disruption of the regular heart rhythm can be caused by one or multiple regions of the heart that alter the normal conduction circuits. These abnormal activation patterns can result in inefficient contraction of the cardiac muscle, which can result in poor blood delivery to the body and damage to vital organs.

Heart rhythm disorders can be treated by ablating the origin of abnormal activation. Clinical diagnosis of arrhythmias can be based at least in part on the analysis of electrocardiograms (ECG) to determine the origin of activation. However, certain ECGs can have an insufficient spatial resolution, and thus can be unsuitable to accurately locate the source of an arrhythmia. Certain invasive electroanatomical mapping systems can be used by clinicians to locate the arrhythmogenic source. Such techniques can include probing the endocardial wall of the myocardium with a catheter to measure the electrical activity, and the location of the catheter can be triangulated from an electrical or magnetic field. However, this mapping strategy can be time-consuming, operator-dependent, and limited by accessibility of the tissue.

Thus, there is an opportunity for techniques to noninvasively create full maps depicting electromechanical activation.

SUMMARY

The disclosed subject matter provides techniques for noninvasive rendering of cardiac electromechanical activation.

The disclosed subject matter provides methods generating an electromechanical map corresponding to a location of a heart from ultrasound data generated using an ultrasound beam. In certain embodiments, a method can include obtaining ultrasound data including a series of image frames and radio frequency (RF) signals corresponding to the location in the heart and measuring displacements and strains based on the ultrasound data to determine an electromechanical activation in the location. The ultrasound data can be converted into a series of isochrone maps, and the series of isochrone maps can be combined to generate the electromechanical map that illustrates an internal wall structure of the heart. The series of isochrone maps can illustrate the electromechanical activation. In some embodiments, the ultrasound beam can be provided to multiple locations within the heart to acquire data corresponding to multiple apical views of the location.

In certain embodiments, the method for generating an electromechanical map can further include beamforming the RF signals to calculate inter-volumes displacements and strains. The displacements and strains over time can be analyzed to identify zero-crossings of the strain curve, i.e., locations and time points at which the displacements switch direction. Such zero-crossings can be indicative of electromechanical activation. In some embodiments, the disclosed method can further include interpolating the zero-crossings into the series of isochrone maps to show the electromechanical activation over time.

In certain embodiments, the method can further include obtaining an electrocardiography (ECG) signal to align the series of consecutive image frames and RF signals. In non-limiting embodiments, the ultrasound data can be obtained over a duration of one or more cardiac cycles and the electromechanical map can illustrate the electromechanical activation, the displacements, and the strains over the duration of one or more cardiac cycles.

The disclosed subject matter also provides systems for generating an electromechanical map. In certain embodiments, an exemplary system can include an ultrasound source to provide an ultrasound beam to a location of a heart, at least one ultrasound system to obtain ultrasound data including a series of image frames and radio frequency (RF) signals corresponding to the location in the heart, and a processor to determine an electromechanical activation in the location. The processor can determine displacements and strains based on the ultrasound data to convert the ultrasound data into a series of isochrone maps; and to generate the electromechanical map by combining the series of isochrone maps. The electromechanical map can illustrate the electromechanical activation of the corresponding location of the heart and internal wall structures of the heart. In non-limiting embodiments, the processor can identify the zero-crossings of the strains at the location of the heart based on the ultrasound data.

In certain embodiments, the ultrasound system can include a 2D array including a plurality of transducer elements. For example, the ultrasound system can be a 2:1 multiplexer. The ultrasound system can image the heart by performing a diverging imaging sequence and/or a focused wave imaging sequence.

In certain embodiments, the processor can generate a heart model for an electromechanical simulation and an ultrasound simulation based on the series of image frames and radio frequency (RF) signals corresponding to the location in the heart. The heart model can illustrate an activation and a propagation of a cardiac action potential.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A is a series of isochrone maps generated from 4 acquisitions for normal rhythm. The median axis is indicated in red, the dotted lines correspond to the considered transverse slice; FIG. 5B is a diagram illustrating, for each view in FIG. 5A, for the considered slice the radial positions of the walls (e.g., r4L) and the activation time values are extracted and organized in a 3-D matrix, in polar coordinates; and FIG. 5C is a diagram illustrating a linear interpolation around the circumference yields a smooth map.

FIG. 6A is a pseudo-3-D view generated using four 2-D activation maps; and FIG. 6B is a 3-D rendering of the activation map of the left ventricle of a canine in normal sinus rhythm. Black lines indicate the position of the imaging planes. The point of earliest activation is in the septal region. LAT: lateral, SEP: septum, ANT: anterior, POST: posterior.

FIG. 7A is a rendered-3-D view; and FIG. 7B is a 3-D rendering of the activation map of the left ventricle of a canine while pacing from the lateral wall. Black lines indicate the position of the imaging planes. The point of earliest activation is in the lateral wall. LAT: lateral, SEP: septum, ANT: anterior, POST: posterior.

FIGS. 9A-9G are flow charts of electromechanical wave imaging in accordance with one embodiment of the presently disclosed subject matter: ultrasound data including images and radio frequency signal is acquired at an increased-frame rate (FIGS. 9A-9C), the axial displacements (FIG. 9D) and the incremental strains (FIG. 9E) of the heart are calculated, the zero-crossings of the strains indicating the electromechanical activation are detected for each point (FIG. 9F) in order to generate an activation map (FIG. 9G).

FIG. 11A is an electromechanical wave imaging of a canine during normal sinus rhythm at 52 milliseconds (ms); FIG. 11B is an electromechanical wave imaging of a canine during normal sinus rhythm at 122 ms; FIG. 11C is an electromechanical wave imaging of a canine during normal sinus rhythm at 172 ms; FIG. 11D is an electromechanical wave imaging of a canine during normal sinus rhythm at 192 ms; FIG. 11E is an electromechanical wave imaging of a canine during normal sinus rhythm at 292 ms; FIG. 11F is an electromechanical wave imaging of electromechanical activation time of the heart.

FIG. 12A is an electromechanical wave imaging of a canine during apical pacing at 25 milliseconds (ms); FIG. 12B is an electromechanical wave imaging of a canine during apical pacing at 52 ms; FIG. 12C is an electromechanical wave imaging of a canine during apical pacing at 81 ms; FIG. 12D is an electromechanical wave imaging of a canine during apical pacing at 109 ms; FIG. 12E is an electromechanical wave imaging of a canine during apical pacing at 136 ms; FIG. 12F is an electromechanical wave imaging of a canine during apical pacing at 165 ms; FIG. 12G is an electromechanical wave imaging of electromechanical activation time of the heart; FIG. 12H is an electrical activation map of the epicardium obtained from electro-anatomical mapping; and FIG. 12I is a picture of the heart with the pacing electrode. The ECG is shown, with the corresponding time point indicated by a dot. RV: right ventricle, LV: left ventricle, ★: earliest site of activation.

FIGS. 17A-I are EWI isochrones of a 7-year-old female with a left lateral pathway before and after successful radiofrequency ablation.

FIGS. 18A-H are EWI isochrones of a 12-year-old female with a right lateral AP before and after successful radiofrequency ablation.

FIGS. 19A-D are EWI isochrones of a 16-year-old male with a right posteroseptal AP before radiofrequency ablation.

FIGS. 20A-D are EWI isochrones of a 17-year-old female with a fasciculoventricular AP prior to catheter ablation.

FIGS. 21A-C are correlation heat maps comparing EWI and ECG pathway localizations to intracardiac results.

FIGS. 23A-D are example EWI isochrones in ventricular and atrial arrhythmias.

FIGS. 25A-B are example EWI isochrones of CTI and mitral flutter.

FIG. 28 is a segmented map of the heart in accordance with the disclosed matter.

FIGS. 29A-E are example EWI isochrones of a posteroseptal AP.

FIGS. 30A-G are example EWI isochrones of a sinus beat and its consecutive PVC beat prior to catheter ablation.

FIGS. 34A-C illustrate 3D-rendered EWIs in an open-chest canine with five different LV pacing locations.

DETAILED DESCRIPTION

Figure 1:
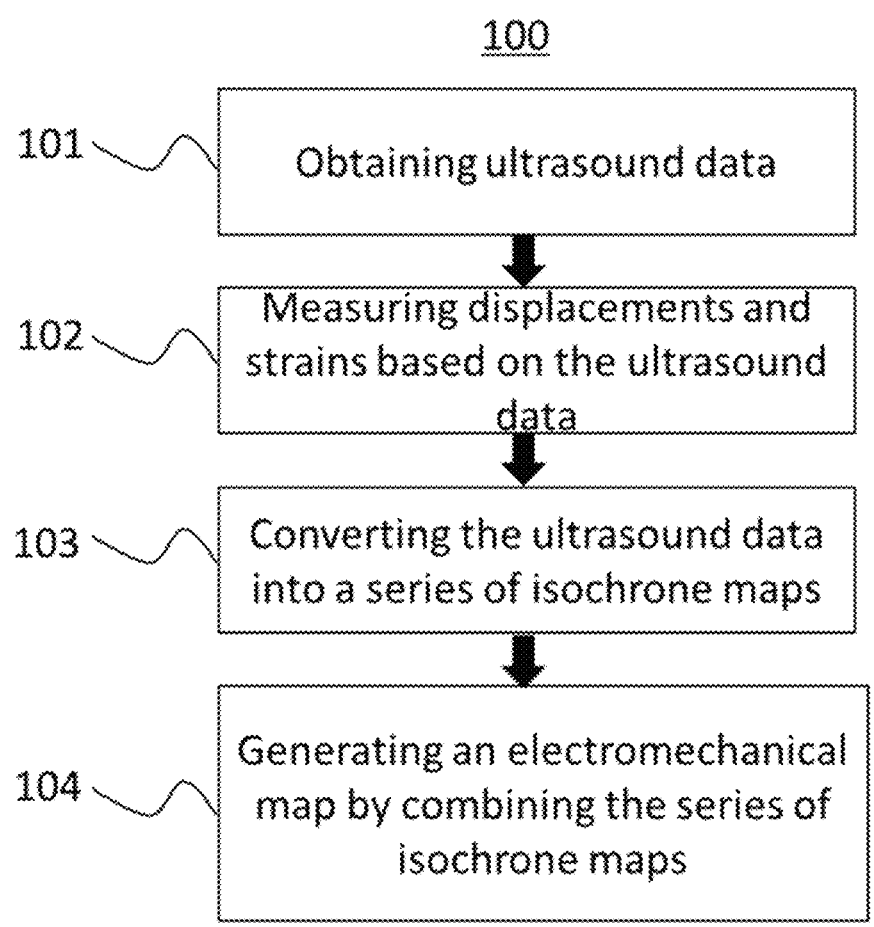
FIG. 1 is a diagram illustrating exemplary stages in a method in accordance with the disclosed matter.
Figure 2:
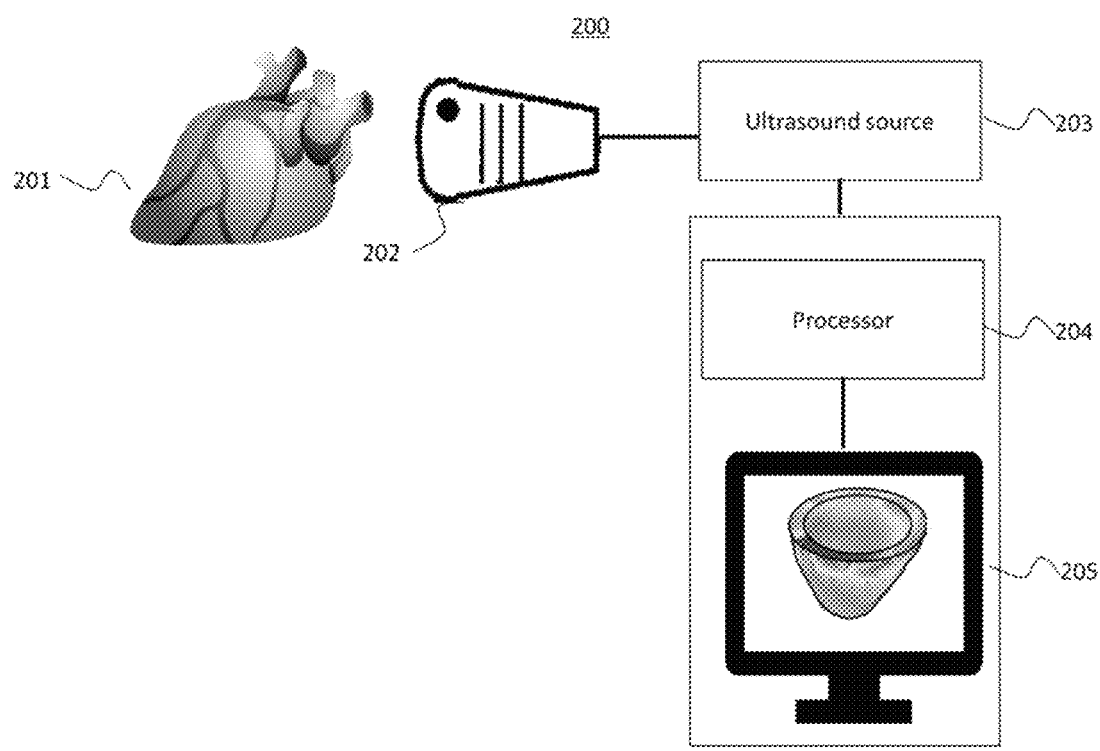
FIG. 2 is a diagram illustrating an exemplary system in accordance with the disclosed matter.

Techniques for the non-invasive rendering of cardiac electromechanical activation are disclosed herein. The presently disclosed systems and methods can generate a 4-D representation of electromechanical activation in a region of the heart, e.g., a cardiac chamber, using non-invasive techniques such as ultrasound.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The terms "comprise(s)," "include(s)," "having," "has," "can," "contain(s)," and variants thereof, as used herein, are intended to be open-ended transitional phrases, terms, or words that do not preclude additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

A "subject" herein can be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc.

In certain embodiments, the method for generating the electromechanical map can further include obtaining ultrasound data comprising a series of consecutive image frames and radio frequency (RF) signals corresponding to a location in the heart 101. An ultrasound beam can be provided to at least one location within the region of the heart to acquire data corresponding to multiple apical views of the region. For example, in certain embodiments, the methods can include acquiring up to 4 apical views. The ultrasound can be configured with an echographic system to acquire and record wave images. For example, a custom-made 2D array of 32×32 ultrasound elements at 3 MHz center frequency and with a pitch of 0.3 mm can be used for 4D ultrasound imaging. The 2D array, which can have a total of 1024 transducer element, can be connected to at least one ultrasound system, each of which has 256 channels. In order to use all the elements of the 2D array, a 2:1 multiplexer can be used for switching from one half of the array to the other half. In some embodiments, diverging and/or focused wave imaging sequences can be used to image the heart. The ultrasound probe can be positioned to acquire apical views of the heart and fixed to a support to maintain the same echocardiographic view for diverging and focused acquisitions. For example, for diverging wave imaging, an ultrasound source 203 can be placed 4.8 mm behind the surface of the transducer to allow for increased volume-rate imaging. The first and the second halves of the 2D array aperture can be used alternatively for each transmit-receive event at a pulse repetition frequency of 1000 Hz. Two consecutive transmit-receive events using each half of the aperture were can be used to reconstruct an entire image, yielding an imaging rate of 500 volumes per second. The ultrasound channel data can be acquired during 2 s.

As embodied herein, the wave images can be acquired and recorded at an increased frame rate, e.g., of about 2000 frames per second. Additionally, an anatomical imaging sequence can be performed in conjunction with providing the ultrasound. In non-limiting embodiments, electrocardiography (ECG) can be performed simultaneously with the ultrasound imaging. For the purpose of example and not limitation, ECG signals can be used to temporally align the increased frame rate wave images with the anatomical images.

In certain embodiments the method for generating the electromechanical map 100 can further include measuring displacements and incremental strains based on the ultrasound data to determine an electromechanical activation in the location 102. The methods can include determining displacements in the contour of the region and generating displacement maps therefrom. Then, the method can include comparing the displacements over time to identify zero-crossings of the strain curve, i.e., locations and time points at which the displacements switch direction. Such zero-crossings can be indicative of electromechanical activation. For example, delay-and-sum beamforming, with a predetermined axial sampling (e.g., 32.1 µm), a predetermined sector angle (e.g., 90°), and a density of one line per degree in both lateral and elevational directions can be performed. 1-D (axial) normalized 1oss-correlation (e.g., 5 mm window, 70% overlap) of beamformed RF signals can be used to estimate inter-volumes displacements. The axial inter-volume strains can be obtained using a least-squares estimator. The axial inter-volume strains can be mapped to volume of voxels (e.g., 256×256×256 voxels).

In certain embodiments, the generated volumes depicting the activation times of the heart overlaid on realistic anatomy can subsequently be used to quantify the speed of the electromechanical wave. This speed can be related to the conduction velocity, a parameter describing the speed and direction of propagation of the action potential wavefront through the myocardium. The conduction velocity provides information about the underlying tissue: slow conduction indicates a tissue in a more diseased state. The conduction velocity can be estimated from data obtained with microelectrode arrays, with optical mapping or clinically with electrogram or electroanatomic mapping systems. For example, the conduction velocity can be estimated by following process: first, a thresholding algorithm can be applied to the generated 3-D EWI volume to create a series of activation maps. These maps can indicate the points being activated at a given time. Second, for each activated site, the active neighborhood is detected and fitted by a smooth polynomial surface using a least square algorithm. Mathematically, the activation timing measurements $t_{act}(xi,yi,zi)$ are approximated by $\hat{t}_{act}(xi,yi,zi)=ax^2+by^2+cz^2+dxy+exz+fyz+gx+hy+iz+j$. Third, the gradients of $\hat{t}_{act}$ can be used to calculate the x, y and z components of the electromechanical wave velocity for this activated neighborhood. Since one point can be part of different fits, a weighted average can be calculated from all the velocity estimates obtained from each fit including the considered point.

In non-limiting embodiments, for in vivo imaging, segmentation can be performed from focused 2D ultrasound images acquired after the diverging wave imaging sequence. For example, focused 2D image acquisitions can be performed using the 2D a aperture and by steering the focused beam in the lateral direction over a 90° sector angle with a beam density of one line per degree. The epicardial and endocardial contours, as well as the atrial and ventricular septum, can be segmented from the 2D ultrasound image. In some embodiments, the segmentation in the elevational direction can be performed by assuming central symmetry of the left atria and ventricle and of the epicardial and endocardial contours at each depth. By orienting the transducer in the apex-to-base direction, the direction of propagation of the ultrasound beam can be aligned with the longitudinal direction of the heart.

In certain embodiments, the method for generating the electromechanical map 100 can further include converting the ultrasound data into a series of isochrone maps, wherein the series of isochrone maps illustrate the electromechanical activation of the corresponding location of the heart 103. Data acquired for each of the apical views can be converted into an isochrone map corresponding to each apical view. For example, the isochrone map can illustrate the electromechanical activation of the region of the heart over time, as observed from a particular apical view. In non-limiting embodiments, the isochrone map can be generated by interpolation of the zero-crossings to show electromechanical activation over time. The onset of longitudinal shortening, resulting from electrical activation, can be determined by the time of first positive-to-negative zero-crossing of the axial strain curves after a reference time point and be defined as the electromechanical activation time. For example, a random selection of 1,000,000 voxels from the reconstructed myocardial volume can be performed and for each voxel selected, the time of first positive-to-negative crossing after the reference time point can be automatically computed. During normal sinus rhythm, the reference time point can be set to the onset of the P-wave for voxels located in the atria and to the onset of the QRS complex for voxels located in the ventricles. During ventricular pacing, the reference time point can be set to the time of pacing. The electromechanical activation times can be linearly interpolated in the myocardial volume to obtain the electromechanical activation map or isochrone. The in vivo electromechanical map can be replicated for two consecutive cardiac cycles.

In certain embodiments, the method for generating the electromechanical map 100 can further include combining the series of isochrone maps to generate the electromechanical map 104, wherein the electromechanical map illustrates internal wall structures of the heart. For example and not limitation, the two or more isochrone maps can be aligned and scaled prior to combination. In certain embodiments, a first isochrone map corresponding to a first apical view is used as a reference image. A dimension of the reference image, e.g., corresponding to a dimension of the region of the heart such as the width of a ventricle, is measured. The second isochrone map corresponding to the second apical view can be scaled to ensure that this dimension is constant across the multiple isochrone maps. The method can further include defining a z-axis that transcends the region of the heart and determining the electromechanical activation at points relative this z-axis and corresponding to the walls of the region of the heart. For each radial position along the z-axis, electromechanical activation and distance from the z-axis can be determined from each of the isochrone maps. By combining these electromechanical activations and distances along the length of the z-axis, the data for the different radial positions can be interpolated into a single, 4-D rendering.

As embodied herein, Electromechanical Wave Imaging (EWI) can be utilized for generating the electromechanical maps. The EWI is an ultrasound-based method that can non-invasively characterize the electromechanical activity of the heart, i.e., the time at which a point of the myocardium starts contracting after being electrically activated. EWI can include following: (1) the minute displacements and the incremental strains of the myocardium can be estimated using increased-frame rate echographic acquisitions and RF-speckle-tracking techniques; and (2) the temporal evolution of the strain can be analyzed in each point of the myocardium to determine the electromechanical activation time. EWI can map the activation sequence of the myocardium in the four chambers of the heart of human and canine models in normal rhythm or pace, of locating pacing sites, and of characterizing and mapping focal arrhythmias. The electromechanical propagation in a beating heart is a complex 3-D phenomenon. EWI can be applied to different standard echocardiographic views (e.g., 4-chamber, 2-chamber, 3-chamber apical views). The resulting 2-D maps are then imported for creating a pseudo-4-D view. Thus, in order to fully visualize the complex 4-D pattern of activation, several 2-D views are acquired and processed separately and then manually registered with a 4-D rendering software to generate the pseudo-4-D view.

In certain embodiments, the disclosed subject matter can provide an electromechanical heart model, including an electrophysiological model and a mechanical model. The electrophysiological model can illustrate the activation and propagation of cardiac action potentials by using a reaction-diffusion partial differential. The mechanical model can illustrate the heart deformation by the balance-of-force equation in which the active contraction force of myofilaments drives the cyclic heart motion. The electrophysiological and mechanical models can be coupled at the cellular level: the membrane ionic kinetics regulates the intracellular calcium transient, which dictates myofilament contraction. The electromechanical simulation can be conducted based on an MRI-image-based finite element human heart model with rule based fiber structures, with the myocardial tissue regarded as an orthotropic, hyperelastic, and nearly-incompressible material. The simulation result can show the deformation of a human heart without and with infarct, both during sinus rhythm. In non-limiting embodiments, the inter-volume axial (apex-to-base direction) displacements obtained from the mechanical finite-element simulation can be sampled, with of 1.8 ms between samples.

In some embodiments, the ultrasound simulation program can be used to generate the ultrasound radio-frequency channel signals with a simulated transducer and a distribution of scatterers. The scatterers can be uniformly distributed at random positions in the ventricles, which geometry is obtained from the mechanical finite-element simulation at each sample. In order to perform 4D ultrasound imaging, a 2D array of 32×32 transducer elements, with an inter-element spacing (or pitch) of 0.3 mm and a center frequency of 3 MHz can be simulated. Increased volume-rate imaging can be achieved by using parallel beamforming with diverging wave imaging, for which the entire volume can be reconstructed from a single transmitted beam. For example, the emission of a spherical wavefront with a transmit angle aperture of 90° can be achieved by placing a virtual source 4.8 mm behind the surface of the transducer. In certain embodiments, a delay-and-sum algorithm can be used to reconstruct the image with an axial sampling of 32.1 μm, a sector angle of 90° and a density of one line per degree in both lateral and elevational directions. The scatterers can be displaced according to the displacement field obtained from the mechanical finite-element simulation at each time sample. The ventricles were imaged at each sample (1.8 ms) during an entire heartbeat, which entails an imaging rate of 556 volumes per second.

In certain embodiments, the disclosed subject matter provides a technique to noninvasively map myocardial activation of the full heart in a single heartbeat throughout all four chambers in 4D (3D over time). This technique can image cardiac deformation resulting from electrical activation with increased frame-rate (500-2000 frames per second) ultrasound to derive the electromechanical activation of the heart. The propagation of myocardial shortening can be described as an electromechanical wave, as it consists of mechanical deformations directly resulting from their local, respective electrical activations. An activation map obtained from this technique can be used as a surrogate for cardiac electrical mapping. Furthermore, this technique can allow linking the electrical and mechanical functions of the heart. Such linking can have clinical value. In some embodiments, the disclosed technique provides a 4D increased frame-rate ultrasound technique to image the propagation of the electromechanical wave and derive the activation map throughout all four chambers simultaneously.

As embodied herein, the 4-D rendering can visualize electromechanical activation across the full thickness of the myocardium, within the epicardium only, or within the endocardium shell. The rendering can provide a complete 4-D visualization of the region of the heart and the be simpler for the clinician to study and interpret. In certain embodiments, the 4-D rendering can be obtained in real-time. Alternatively, the data can be acquired in real-time and the 4-D rendering can be performed later. In certain embodiments, the heart of the subject can be in normal sinus rhythm. Alternatively, the heart of the subject can be paced, e.g., using a pacing signal from an electrode.

In certain embodiments, the disclosed subject matter can provide a technique to diagnosis a specific arrhythmia condition. For example and not limitation, the ultrasound data can be obtained from a heart of a subject for diagnosing and treating a Wolff-Parkinson White (WPW) condition. Alternatively, the ultrasound data can be obtained from a heart of a subject for diagnosing and treating a Pre-Ventricular Contraction (PVC) condition. As shown in FIGS. 15A-15D, the heart with WPW or PVC can be rendered into 2D and 3D isochrone maps with electromechanical activation time.

In certain embodiments, an exemplary embodiment of the system 200 can include an image detection device 202, such as ultrasound probe or system, which is used to create images of the heart 201 or other organ or structure of a subject. The image detection device does not induce discernible vibration in the body structure and merely detects pre-existing motion. The signals detected by the probe can be transferred to an ultrasound system 202. The image detection device can be connected to an ultrasound source 203. The ultrasound source can provide at least one ultrasound beam to the heart 201 or other organs. The ultrasound beam can be provided to multiple locations within the heart to acquire data corresponding to multiple apical views of the location. In some embodiments, the ultrasound source 203 can provide an ultrasound beam for diverging and focused acquisitions.

In some embodiments, an exemplary embodiment of the system can include a processor 204. The raw data produced by the system 202 can be transferred to a processor 204 which is configured to generate the electromechanical map by calculating a displacement and incremental strains based on the series of image frames and RF signals. The processor 204 can determine an electromechanical activation in the location by calculating displacements and strains based on the ultrasound data, convert the ultrasound data into a series of isochrone maps; and generate the electromechanical map by combining the series of isochrone maps. In the exemplary embodiment, the processor 204 can be integrated with the ultrasound system 202.

In some embodiments, the system can include storage devices such as disk drives, for storing data on input files and for writing output onto output files. As will be described herein, input files can include information such as thresholds. Output files can include the displacement maps, videos of myocardium displacements, or computed data, such as electromechanical wave properties. In some embodiments, the system can include an output device 205, such as to monitor, and an input device, such as keyboard.

In certain embodiments, the disclosed subject matter provides techniques to improve spatial imaging resolution of EWI. For example, spatial imaging resolution for arrhythmia localization can be improved by increasing the number of multi-2D slices. With the more multi-2D slices for sampling, the earliest activated region after interpolation can be more focal, and the distance computed from the 3D-rendered isochrones between the pacing electrodes can be closer to the true values measured on the surface of the heart.

In certain embodiments, the disclosed techniques can be used to visualize cardiac electromechanical activation based on an ultrasound sequence. For example, the disclosed subject matter can provide EWI techniques to localize accessory pathways (APs) in pediatric patients. For example, the disclosed EWI can locate APs in pediatric patients and provide information to clinical electrophysiologists prior to catheter ablation procedures. In non-limiting embodiments, the disclosed EWI isochrones can also provide anatomical visualization of ventricular pre-excitation.

In certain embodiments, the disclosed techniques can provide non-invasive clinical tools to diagnose and localize cardiac arrhythmias. For example, the disclosed EWI techniques can be used to non-invasively map the electromechanical activation of atrial and ventricular arrhythmias in adult patients. In non-limiting embodiments, the disclosed EWI techniques can be used for localization of various arrhythmias in all four chambers of the heart prior to catheter ablation. Patients can have an accessory pathway (AP) in WPW syndrome, PVC, atrial tachycardia (AT), and/or atrial flutter (AFL). In some embodiments, the disclosed EWI techniques can reduce the effects of inter-observer variability (e.g., different interpretations by experts/physicians).

Example 1: A 3-D Rendering Algorithm for Electromechanical Wave Imaging of a Beating Heart This Example illustrates the use of the disclosed technique for generating a non-invasive cardiac electromechanical map using multiple 2-D images. Two canine models were considered to illustrate the technique: one in normal sinus rhythm and one-paced from the lateral region of the heart. Four standard echographic views of each canine heart were acquired. Electromechanical Wave Imaging was applied to generate four 2-D activation maps of the left ventricle. The radial positions and activation timings of the walls were automatically extracted from those maps. In each slice, from apex to base, these values were interpolated around the circumference to generate a full 3-D map.

In both cases, a 3-D activation map and a cine-loop of the propagation of the electromechanical wave were automatically generated. The 3-D map showing the electromechanical activation timings overlaid on realistic anatomy assists with the visualization of the sources of earlier activation (which are potential arrhythmogenic sources). The earliest sources of activation corresponded to the expected ones: septum for the normal rhythm and lateral for the pacing case. Thus, the presently disclosed techniques provide, automatically, a 3-D electromechanical activation map with realistic anatomy. This represents a provision towards a non-invasive tool to efficiently localize arrhythmias in 3-D.

Materials and Methods

Protocol:

Two male adult mongrel canines (weight=22 and 24.5 kg) were used. They were anesthetized with an intravenous injection of Propofol (2-5 mg·kg$^{-1}$). During the procedure, the animals were positioned supine on a heating pad and mechanically ventilated with a rate- and volume-regulated ventilator on a mixture of oxygen and isoflurane (0.5-5%). The chest was opened by left lateral thoracotomy with electrocautery and the heart was exposed by removing a rib. The heart of one canine was imaged with ultrasound while in normal sinus rhythm. The heart of the second animal was imaged while externally paced: a bipolar electrode was sutured onto the epicardial wall, in the lateral area of the left ventricle; this electrode was connected to a data acquisition system (NI USB-6259, National Instruments, Austin, Tex.), which sent a pacing signal (amplitude 10 V, pulse width 2 ms, cycle length 500 ms). For acoustic impedance matching purposes, the thoracic cavity was filled with saline during ultrasound acquisitions.

Figure 3A:
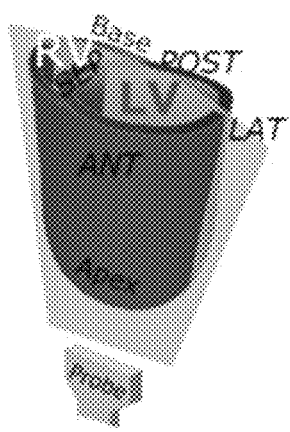
FIG. 3A is a diagram illustrating ultrasonic acquisition of a 4-chamber view of the heart, depicting the left and right ventricles.
Figure 3B:
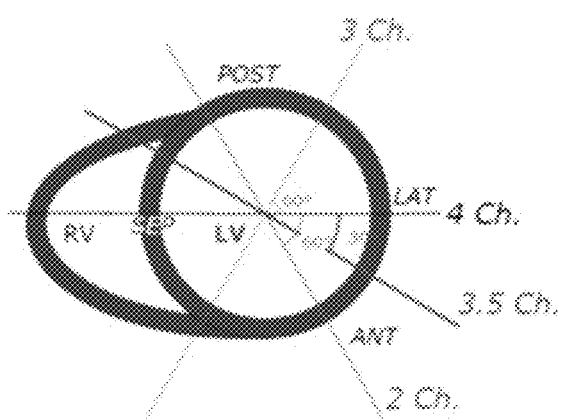
FIG. 3B is a diagram illustrating a view from the heart base of the relative positions of the four planes of imaging.
Figure 3C:
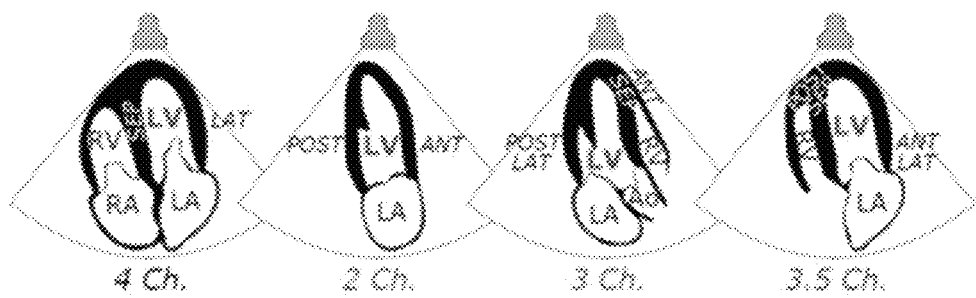
FIG. 3C is a series of schematic diagrams of the heart chambers as seen in the four different echocardiographic views. (RV/LV: right/left ventricle, RA/LA: right/left atrium, Au: aorta, LAT: lateral, SEP: septum, ANT: anterior, POST: posterior.)

Ultrasound Acquisition:

The RF channel data were acquired using a 2.5 MHz center frequency phased array (P4-2 ATL/Philips, Andover, Mass., US) connected to a research echographic system (V-1 Verasonics, Kirkland, Mass., US). Diverging wave imaging was used to achieve a frame rate of 2000 frames per second. Two-second acquisitions were recorded to ensure visualization for at least one cardiac cycle. This increased frame rate acquisition was followed by an anatomical imaging sequence (standard 64-line B-mode with 30 fps). The ECG signal recorded synchronously with ultrasound data using an ECG unit (77804A, HP, Palo Alto, Calif., US) was used to temporally align the increased frame rate data with the anatomical images. Four different apical views were acquired for each canine: three standard echographic views and one custom-defined view. The first view is the "4-chamber" view: the probe is placed at the apex of the heart and rotated until the four chambers (two atria and two ventricles) are optimally visualized. This view serves as a reference: a counterclockwise rotation of 60° of the transducer yields the "2-chamber" view (left atrium and left ventricle) while a clockwise rotation enables visualization of the "3-chamber" view (left atrium and left ventricle, right ventricle). An extra view, called "3.5-chamber" view, is acquired between the "4-chamber" and the "2-chamber" planes. The orientations of these different views are depicted in FIG. 3.

Figure 4:
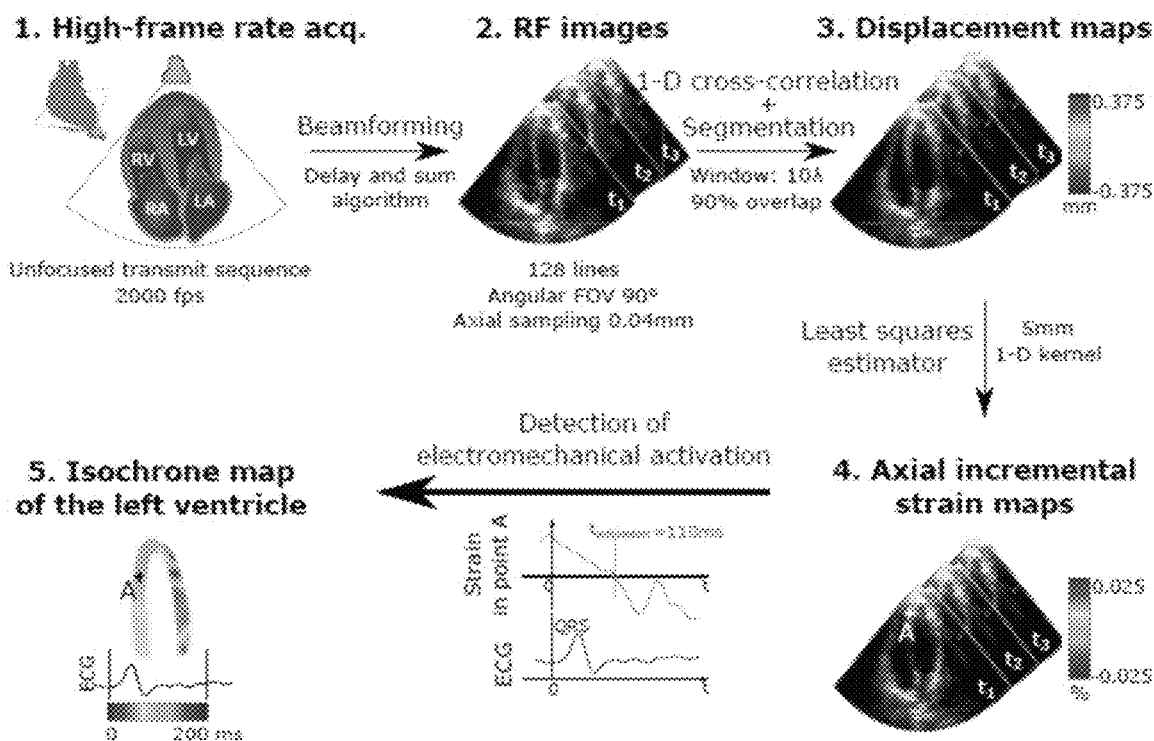
FIG. 4 is a diagram illustrating the EWI algorithm in accordance with an exemplary embodiment of the disclosed subject matter: 2-D images of the heart are acquired at an increased frame rate, the axial displacements and the incremental strains of the myocardium are estimated, the zero-crossings of the strains indicating the electromechanical activation are detected for each point in order to generate an activation map.

Electromechanical Wave Imaging:

The RF data were processed independently for each echocardiographic view with the EWI technique (FIG. 4). A delay-and-sum algorithm was used to reconstruct the series of RF images from the signals received by the elements of the phased array. These beam-formed images present a field of view of 90° for 128 lines (i.e., an angular sampling of 0.7°). The axial sampling frequency was 20 MHz (i.e., an axial sampling of 0.0385 mm). Axial displacements were estimated between successive RF frames using a fast 1-D RF-based cross-correlation algorithm with a window length of 10λ, (6.2 mm) and an overlap of 90%. The contour of the myocardium was manually segmented on the first frame of the anatomical imaging sequence. Subsequently, the estimated displacements were used to automatically track the contour throughout the cardiac cycle. Axial incremental strains in the myocardium were calculated between consecutive RF frames using a least-squares estimator with a 5 mm-kernel. Strains characterize the mechanical behavior of the myocardium: positive strains reflects a lengthening while negative strains indicate a shortening of the tissue. The electromechanical activation of a point of the heart thus corresponds to a change of sign, i.e., a zero-crossing of the strain curve (positive-to-negative or negative-to-positive according to the orientation of the tissue). An isochrone map depicting the electromechanical activation in each point of the myocardium was generated by detecting the time of occurrence of the first zero-crossing after the onset of the electrical activation (beginning of the QRS). The zero-crossings were semi-manually obtained in 60 to 100 randomly selected regions. Cubic interpolation was then used to generate a smooth continuous isochrone map. This process was repeated for each of the four acquired views. Although this method can be applied to map the electromechanical activation in the four chambers of the heart, this focused on the left ventricle only (LV).

Creation of a 3-D Electromechanical Activation Map:

The four isochrone maps served as an input to a custom-made algorithm (Matlab, The Mathworks, Inc., Natick, Mass., US) to generate a 3-D activation map. Three hypotheses were made to create the 3-D map: (i) the different views are organized as in the theoretical case, FIG. 3; (ii) the apical points and the median axes on the four different views are collocated and correspond to the apical point and the median axis of the 3-D matrix; and (iii) the width of the left ventricle at the mid-level is the same in the four different acquisition planes.

The algorithm started with the detection of the median axis of one of the 2-D views, referred to as z-axis. The width of the ventricle was measured at the mid-level in each view and if necessary, the images were rescaled to comply with the hypothesis (iii). Then, for each position along this z-axis, a search on the perpendicular axis was performed to detect the location (i.e., the radial distance from the z-axis) and the activation time values of the points of the walls (FIG. 5(a)). These activation time values were written in a 3-D matrix at a position defined by the polar coordinates: calculated radius, theoretical angle (depending on the considered view), and altitude z on the z-axis. The detection of the radius and activation time was repeated in the four different views for the same z-axis value. For a given z value, the 3-D matrix thus had eight series of values spread around a more or less circular section (FIG. 5(b)). For each radial position, a linear interpolation between these eight different points yielded a smooth profile around the circumference (FIG. 5(c)). These were repeated for each z position, i.e., for each slice of the heart from the apex to the base, resulting in a 3-D matrix describing the geometry and the electromechanical activation times. The 3-D matrix was finally transformed from polar coordinates to cartesian coordinates. Using the same algorithm, the user can choose to visualize the full thickness of the myocardium or only the epicardium or endocardium shell. The location of the four initial echographic views was saved in a different 3-D matrix.

The resulting 3-D matrices were visualized in Amira 5.3.3 (Visage Imaging, Chelmsford, Mass., US) using commercial volume rendering algorithms. A standard physics colormap was used to visualize the 3-D maps. A monochromatic map and a thresholding method were used to create a movie of the EW propagation.

For comparison purposes, the previously-used pseudo-3-D views were constructed. The four 2-D activation maps corresponding to the four echocardiographic acquisitions were manually co-registered in Amira 5.3.3 using anatomical landmarks (i.e., the position of the apex). The resulting psuedo-3-D view is provided in FIG. 6(a).

Results

Figure 8A:
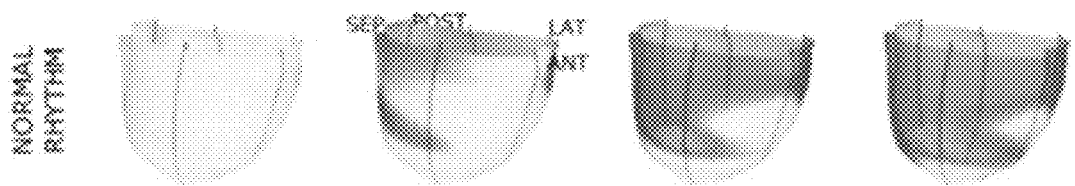
FIG. 8A is a snapshot of a video of the EW propagation in the left ventricles of a canine in normal sinus rhythm.
Figure 8B:
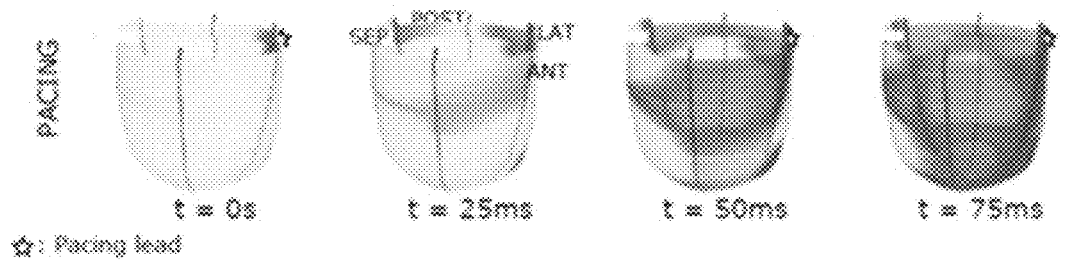
FIG. 8B is snapshot of a video of the EW propagation in the left ventricles of a canine in pacing from the lateral wall. Black lines indicate the position of the four planes of imaging.

The 3-D rendering method in accordance with the disclosed subject matter was applied to data acquired on a canine heart in normal sinus rhythm. The algorithm is illustrated for one slice along the z-axis of this case in FIG. 5. The resulting shell is presented FIG. 6(b), alongside the pseudo-3-D view, FIG. 6(a). The same process was applied to data acquired on a canine heart paced from the antero-lateral wall. The resulting 3-D matrix and the pseudo-3-D view are presented in FIG. 7. Snapshots of the movies of activation are presented in FIG. 8 for normal sinus rhythm, (a), and paced rhythm, (b). For visualization purposes, the propagation is depicted on the epicardial shell rather than on the full myocardial matrix.

Discussion

Thus, this Example demonstrates that the presently disclosed subject matter provides methods and systems to visualize the electromechanical activation of the myocardium in 3-D in a chamber of the heart. The method was applied in two cases with different activation patterns (a canine in normal sinus rhythm and a canine paced from the lateral wall) and was compared to the previous pseudo-3-D rendering technique.

The proposed method is fully automated while the pseudo-3-D views are generated manually. As such, the new technique is time-efficient (5 min vs.~15-30 min) and not operator-dependent. Moreover, the resulting 3-D image offers structural information of clinical utility overlaid on realistic anatomy. This electromechanical activation shell is thus easier for the clinician, to interpret than the pseudo-3-D map.

The electromechanical activation patterns depicted by the pseudo-3-D and the 3-D maps correspond to the expected electrical activation sequence for the two studied situations. For the normal sinus rhythm case, the electrical signals are generated spontaneously at the sinus node, in the right atrium. The signals travel through the atrium, the atrioventricular node, the bundle of His and finally through the ventricular myocardium, following the Purkinje fiber network. In the ventricle, the activation pattern is complex, originating from multiple locations depending on the fiber network. This theoretical description is illustrated in the 3-D map (FIG. 6) and the movie (FIG. 8(a)), which show that: (i) an earlier activation is noticed in the base-middle part of the ventricle, compared to the apex; (ii) the point with the earliest activation is located in the septum; and (iii) multiple points located in different regions (septum, posterior, lateral) of the heart are activated at the same time. For the paced rhythm model, the activation pattern is simpler: the EW can originate from a single point, the pacing lead. In the case studied, the pacing lead was placed in the basal region of the lateral wall. The region of the earliest activation indeed coincided with the position of the lead (FIGS. 7 and 8(b)).

In conclusion, the proposed 3-D rendering method represents a non-invasive, fully automated characterization of the electromechanical activation of the whole heart in real-time. The 3-D rendering algorithm to generate electromechanical activation maps of the left ventricle of a beating heart has been described herein. This technique was applied to map the activation pattern in two large animal models: normal sinus rhythm and a paced rhythm. The automatically-generated 3-D maps depict in a clear way the propagation of the electromechanical wave and can provide clinicians with an efficient non-invasive tool to characterize arrhythmias.

Example II: 4D Noninvasive Cardiac Electromechanical Activation Mapping

This Example illustrates the use of the disclosed technique for non-invasive 4D mapping of the cardiac electromechanical activity in a single heartbeat. The disclosed technique captured the activation wave throughout all four chambers in vivo. Electromechanical activation maps were presented in a normal and infarcted cardiac model in silico and in a paced canine heart in vivo. Noninvasive 4D electromechanical activation mapping in a human subject was also performed. This noninvasive 4D mapping technique can be readily applied in the clinic for direct visualization of electromechanical activation of the heart at the early onset of heart dysfunction, and thus result in the timely and effective treatment thereof.

Method and Materials

Computer Heart Simulation:

The disclosed electromechanical heart model consists of an electrophysiological model and a mechanical model. The electrophysiological model represents the activation and propagation of cardiac action potentials by using a reaction-diffusion partial differential equation simulated by the software CARP (CardioSolv LLC). The mechanical model describes the heart deformation by the balance-of-force equation in which the active contraction force of myofilaments drives the cyclic heart motion. The electrophysiological and mechanical models were coupled at the cellular level: the membrane ionic kinetics regulates the intracellular calcium transient, which dictates myofilament contraction. The electromechanical simulation was conducted based on an MRI-image-based finite element human heart model with rule-based fiber structures, with the myocardial tissue regarded as an orthotropic, hyperelastic, and nearly-incompressible material. The simulation result describes the deformation of a human heart without and with infarct, both during sinus rhythm. The inter-volume axial (apex-to-base direction) displacements obtained from the mechanical finite-eluent simulation were sampled at 1.8 ms.

The ultrasound simulation program Field II was used to generate the ultrasound radio-frequency channel signals with a simulated transducer and a distribution of scatterers. The scatterers were uniformly distributed at random positions in the ventricles, which geometry was obtained from the mechanical finite-element simulation at each sample. In order to perform 4D ultrasound imaging, a 2D array of 32×32 transducer elements, with an inter-element spacing (or pitch) of 0.3 mm and a center frequency of 3 MHz was simulated. Increased volume-rate imaging was achieved by using parallel beamforming with diverging wave imaging, for which the entire volume can be reconstructed from a single transmitted beam. The emission of a spherical wavefront with a transmit angle aperture of 90° was achieved by placing a virtual source 4.8 mm behind the surface of the transducer. A delay-and-sum algorithm was used to reconstruct the image with an axial sampling of 32.1 μm, a sector angle of 90° and a density of one line per degree in both lateral and elevational directions. The scatterers were displaced according to the displacement field obtained from the mechanical finite-element simulation at each sample. The ventricles were imaged at each sample (1.8 ms) during an entire heartbeat, which entails an imaging rate of 556 volumes per second.

Animal Protocol:

Two male canines (23.6±0.6 kg) were predicated with diazepam (0.2-1 mg/kg) injected intravenously and then anesthetized with an intravenous injection of propofol (2-5 mg/kg). The canines were mechanically ventilated with a rate- and volume-regulated ventilator on a mixture of oxygen and titrated 0.5-5% isoflurane. Lidocaine (30-50 μg/(kg·min)) was injected intravenously throughout the procedure to minimize the occurrence of ventricular arrhythmia. A left lateral thoracotomy was performed with electrocautery and one rib was removed to expose the heart. In one canine, two external bipolar electrodes were sutured onto the epicardial surface of the LV in the vicinity of the apical and lateral regions. The epicardial electrodes were connected to a function generator (AFG3022C, Tektronix, Beaverton, Oreg.), delivering a 2-V amplitude, 2-ms pulse width at a period of 400 ms. Only one electrode at a time was used for pacing. Electroanatomical mapping of the ventricular surface was performed using a bipolar catheter (TactiCath, St. Jude Medical, Saint Paul, Minn.). The 3D position of the catheter was obtained from a navigation system (EnSite Precision, St. Jude Medical, Saint Paul, Minn.) using adhesive sensor patches placed on the canine.

Electromechanical Wave Imaging:

Ultrasound imaging was performed during normal sinus rhythm or epicardial pacing in the open-chest canines and transthoracically during normal sinus rhythm in a healthy human volunteer. A custom-made 2D array of 32×32 ultrasound elements at 3 MHz center frequency and with a pitch of 0.3 mm (Vermon SA, France), identical to the one designed for the ultrasound simulation, was used for 4D ultrasound imaging. The 2D array, which has a total of 1024 transducer element, was connected to two ultrasound systems (Vantage, Verasonics, Kirkland, Wash.), each of which having 256 channels. In order to use all the elements of the 2D array, a 2:1 multiplexer, allowing for switching from one half of the array to the other half was used. Both diverging and focused wave imaging sequences were used to image the canine heart. The ultrasound probe was positioned to acquire apical views of the heart and fixed to a support to maintain the same echocardiographic view for diverging and focused acquisitions. For diverging wave imaging, similarly to the ultrasound simulations, a virtual source was placed 4.8 mm behind the surface of the transducer to allow for increased volume-rate imaging. The first and the second halves of the 2D array aperture were used alternatively for each transmit-receive event at a pulse repetition frequency of 1000 Hz. Two consecutive transmit-receive events using each half of the aperture were used to reconstruct an entire image, yielding an imaging rate of 500 volumes per second. The ultrasound channel data were acquired during 2 s. Standard delay-and-sum beamforming, identical to the one used in the simulation, with an axial sampling of 32.1 μm, a sector angle of 90° and a density of one line per degree in both lateral and elevational directions vas performed. 1-D (axial) normalized cross-correlation (5 mm window. 70% overlap) of beamformed signals was used to estimate inter-volumes displacements. The axial inter-volume strains were obtained using a least-squares estimator implemented with a Savitzky-Golay filter. The axial inter-volume strains were mapped to volume of 256×256×256 voxels. For in vivo imaging, segmentation was performed from focused 2D ultrasound images acquired immediately after the diverging wave imaging sequence. Focused 2D image acquisitions were performed using one-quarter of the 2D array aperture (32×8) and by steering the focused beam in the lateral direction over a 90° sector angle with a beam density of one line per degree while the elevational focus was set to a depth of 70 mm. The epicardial and endocardial contours, as well as the atrial and ventricular septum, were manually segmented from the 2D ultrasound image. The segmentation in the elevational direction was performed by assuming central symmetry of the left atria and ventricle and of the epicardial and endocardial contours at each depth. By orienting the transducer in the apex-to-base direction, the direction of propagation of the ultrasound beam was approximately aligned with the longitudinal direction of the heart. Therefore, myocardial contraction, which is associated with longitudinal shortening, corresponded to negative axial strain. Therefore, local longitudinal shortening was characterized by negative axial strains. The onset of longitudinal shortening, resulting from electrical activation, was determined by the time of first positive-to-negative zero-crossing of the axial strain curves after a reference time point and was defined as the electromechanical activation time. A random selection of 1,000,000 voxels from the reconstructed myocardial volume was performed and for each voxel selected, the time of first positive-to-negative zero-crossing after the reference time point was automatically computed. During normal sinus rhythm, the reference time point was set to the onset of the P-wave for voxels located in the atria and to the onset of the QRS complex for voxels located in the ventricles. During ventricular pacing, the reference time point was set to the time of pacing. The electromechanical activation times were then linearly interpolated in the myocardial volume to obtain the electromechanical activation map or isochrone. The in vivo electromechanical map was replicated for two consecutive cardiac cycles.

Results 4D, increased-volume-rate EWI can map the electromechanical activation of the entire heart noninvasively and in a single heartbeat (FIGS. 9A-9G). The heart was first imaged in the apical view with 4D ultrasound using emission of diverging acoustic waves to achieve increased volume-rate imaging. Inter-volume axial displacements and strains were subsequently estimated, and the local onset of contraction was defined by the time of first positive to negative zero-crossing of the temporal axial strain curve at a given location. The electromechanical activation map was then obtained by determining the local onset of contraction for each voxel of the myocardium. Validation of the electromechanical maps was performed, in silico against electrical maps and in vivo against the clinical gold-standard, i.e., electroanatomical mapping. Proof-of-concept of this technique was finally shown transthoracically in a normal human subject in vivo.

In Silico EWI of Human Hearts

Figure 10A:
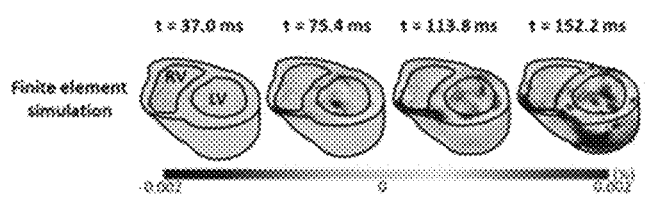
FIGS. 10A and 10B are axial strain images obtained from benchmark mechanical finite-element simulation in the infarct-free baseline.
Figure 10B:
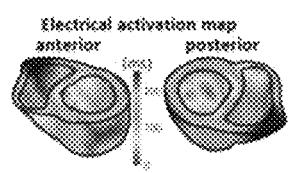
Figure 10C:
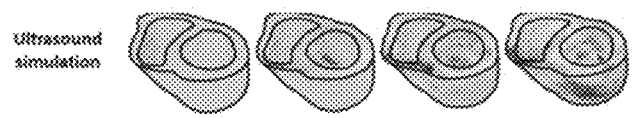
FIGS. 10C and 10D are axial strain images estimated from increased frame-rate 4D ultrasound simulation in the infarct-free.
Figure 10D:
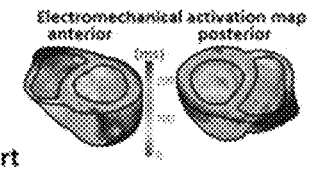
Figure 10E:
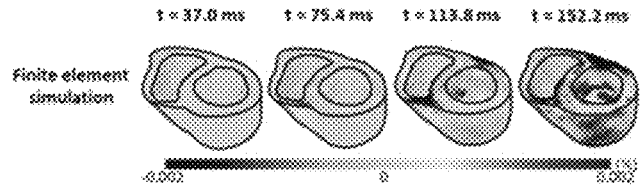
FIGS. 10E and 10F are axial strain images obtained from benchmark mechanical finite-element simulation in infarcted hearts.
Figure 10F:
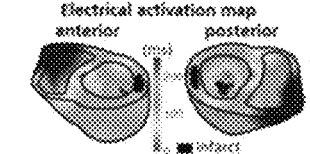
Figure 10G:
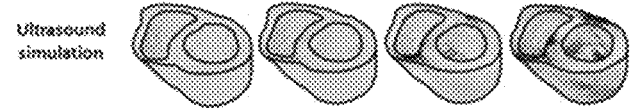
FIGS. 10G and 10H are axial strain images estimated from increased frame-rate 4D ultrasound simulation in infarcted hearts, in the right (RV) and left (LV) ventricles at different time points are shown.
Figure 10H:
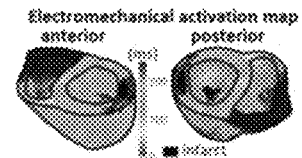

To demonstrate the feasibility of 4D EWI, an ultrasound simulation program (Field II) was used in combination with the finite-element electromechanical simulation of a human heart model reconstructed from MRI images. The electrophysiological model represents the activation and propagation of cardiac action potentials by using a reaction-diffusion partial differential equation. The heartbeat was then imaged with 4D ultrasound at 556 volumes per second. Inter-volume axial displacements and strains were estimated from the ultrasound radiofrequency (RF) signals. Ventricular axial strains estimated with ultrasound were compared to their computational equivalents in the infarct-free and infarcted hearts (FIG. 10). Snapshots at different time points after the onset of electrical activation illustrate the propagation of the electromechanical wave. Negative strains, indicating shortening, correspond to myocardial contraction. In the simulated infarct-free heart, early contraction occurs in the ventricular septum, between the right and left ventricles, as well as in the anterior basal region of the right ventricle for (FIG. 10a). Myocardial contraction then propagates in both ventricles. Snapshots of the estimated axial strains (FIG. 10c) were in agreement with their true counterparts (FIG. 10a) as they exhibit a similar pattern. True electrical activation times (FIG. 10b) were also in agreement with the estimated electromechanical activation times (FIG. 10d). The electrical activation maps, or isochrones, exhibited early activation in the septal region, the endocardial layer of the anterior LV, the anterior region at the base of the RV and the posterior-septal region at the base of the LV. The electromechanical activation map obtained from EWI also points these regions as earliest sites of activation. Delayed sites of activation were found in the posterior region of the RV at the basal level, in the epicardial layer of the anterior-lateral region of the LV and in the basal region of the posterior-lateral LV. In the infarcted heart, a similar pattern of electromechanical wave propagation was identified for the benchmark (FIG. 10e) and the estimated (FIG. 10g) axial strains. Agreement was obtained between the true electrical (FIG. 10f) and the estimated electromechanical (FIG. 10h) activation times. The infarct region was not activated.

In Vivo EWI of a Canine During Sinus Rhythm

Feasibility of 4D EWI and cardiac activation mapping in a canine model were assessed. Inter-volume axial strains were imaged during a single heartbeat. Snapshots of the inter-volume axial strains at different time points of the cardiac cycle show the propagation of the electromechanical wave (FIG. 11). The earliest myocardial contraction occurs in the right atrium (FIG. 11a), during the P-wave. The electromechanical wave then propagated to the left atrium (FIG. 11b). After the onset of the QRS complex, early contraction occurred in the ventricular septum (FIG. 11c) and then propagated to both ventricles (FIGS. 11d and e). The propagation of the electromechanical wave was consistent with the ECG, which is a purely electrical measurement of cardiac activity. The electromechanical activation times were mapped in the canine heart (FIG. 11f). The electromechanical activation map obtained with EWI was consistent with the ECG and the known sequence of electrical activation of a normal heart.

In Vivo EWI of a Canine During Electrical Pacing

Figure 13A:
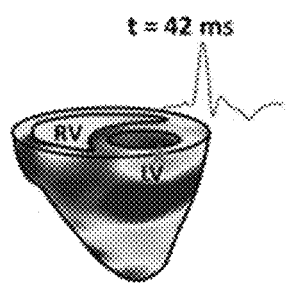
FIG. 13A is an electromechanical wave imaging of a canine during left ventricular (LV) pacing at 42 milliseconds (ms)
Figure 13B:
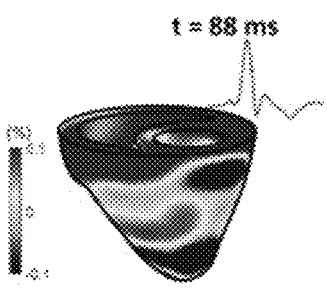
FIG. 13B is an electromechanical wave imaging of a canine during LV pacing at 88 ms.
Figure 13C:
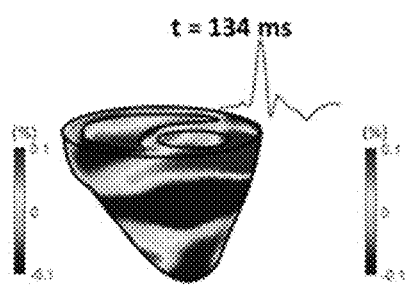
FIG. 13C is an electromechanical wave imaging of a canine during LV pacing at 134 ms.
Figure 13D:
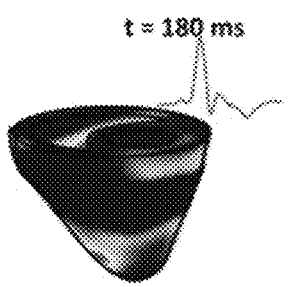
FIG. 13D is an electromechanical wave imaging of a canine during LV pacing at 180 ms.
Figure 13E:
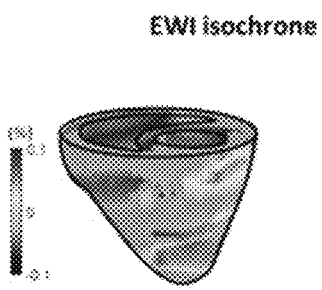
FIG. 13E is an electromechanical wave imaging of electromechanical activation time of the heart.
Figure 13F:
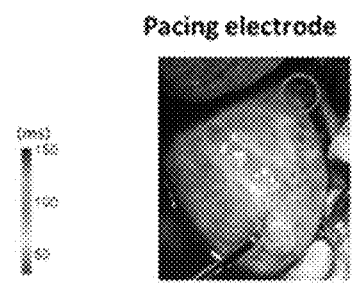
FIG. 13F is a picture of the heart with the pacing electrode. The ECG is shown, with the corresponding time point indicated by a dot. RV: right ventricle, ★: earliest site of activation

Validation of electromechanical mapping was also performed in a canine in vivo. Two pacing electrodes were sutured onto the epicardial surface of the heart: one in the anterior region at the apical level and the other one in the lateral free wall of the LV at the basal level (FIG. 12i). During apical pacing, both ventricles were imaged with increased-volume rate 4D ultrasound in a single heartbeat. After EWI data acquisition, electroanatomical mapping of the epicardial surface was performed using a single electrode mapping catheter which was positioned at various locations of the epicardium that could be reached in the open-chest canine. The earliest region of contraction was found at the apex (FIG. 12a), near the position of the sutured electrode. Then, the electromechanical wave propagated towards the base in both ventricles (FIGS. 12b,c,d,e, and f). FIG. 12f shows that 165 ms after pacing, both ventricles were fully electromechanically activated. The isochronal map obtained from EWI (FIG. 12g) was found to be in agreement with the electrical activation times obtained from electroanatomical mapping (FIG. 12h). The earliest regions of electromechanical and electrical activations are located in the apex, where the electrode was pacing from (FIG. 12i). During lateral LV free wall pacing, increased volume-rate 3D ultrasound images were acquired, and snapshots of the inter-volume axial strains showed the propagation of the electromechanical wave (FIG. 13). Two sites of early contraction were found after pacing: the lateral free wall at the basal level, where the pacing signal was delivered, and the apical region of the lateral wall. The electromechanical wave then propagated to both ventricles and the RV free fall was the last region activated. FIG. 13e shows an isochronal map, where early activation is shown in the LV free wall and late activation in the RV free wall. The position of the pacing electrode at the basal level of the LV (FIG. 13f) is in agreement with early activation in this region.

In Vivo EWI of a Normal Human Heart

Figure 14A:
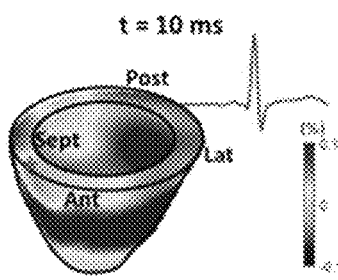
FIG. 14A is an electromechanical wave imaging of a human left ventricle (LV) during normal sinus rhythm at 10 milliseconds (ms)
Figure 14B:
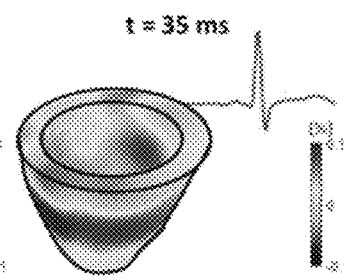
FIG. 14B is an electromechanical wave imaging of a human LV during normal sinus rhythm at 35 ms.
Figure 14C:
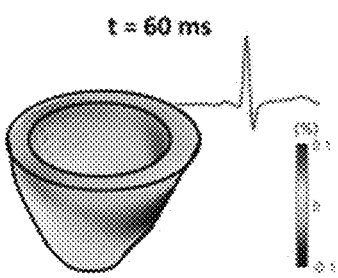
FIG. 14C is an electromechanical wave imaging of a human LV during normal sinus rhythm at 60 ms.
Figure 14D:
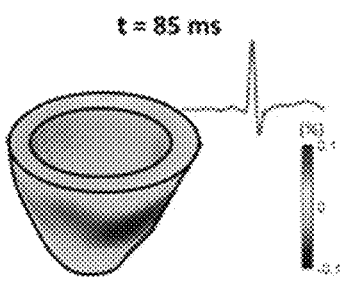
FIG. 14D is an electromechanical wave imaging of a human LV during normal sinus rhythm at 85 ms.
Figure 14E:
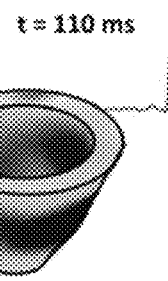
FIG. 14E is an electromechanical wave imaging of a human LV during normal sinus rhythm at 110 ms.
Figure 14F:
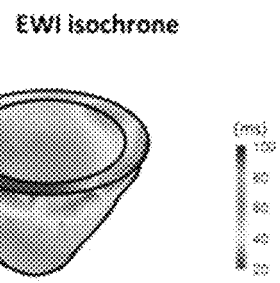
FIG. 14F is an electromechanical wave imaging of electromechanical activation time of the heart. The ECG is shown, with the corresponding time point indicated by a dot. Post: posterior, Lat: lateral, Ant: anterior, Sept: septal, ★: earliest site of activation.
Figure 15A:
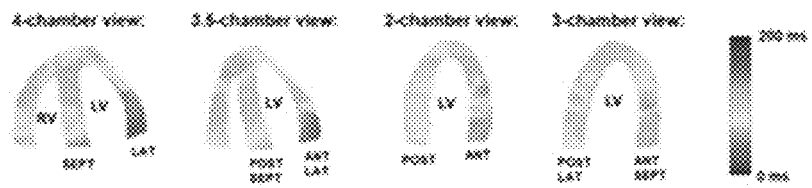
FIGS. 15A and 15B are 2D, and 3D rendered isochrone maps of a heart in a patient with Wolff-Parkinson White (WPW).
Figure 15B:
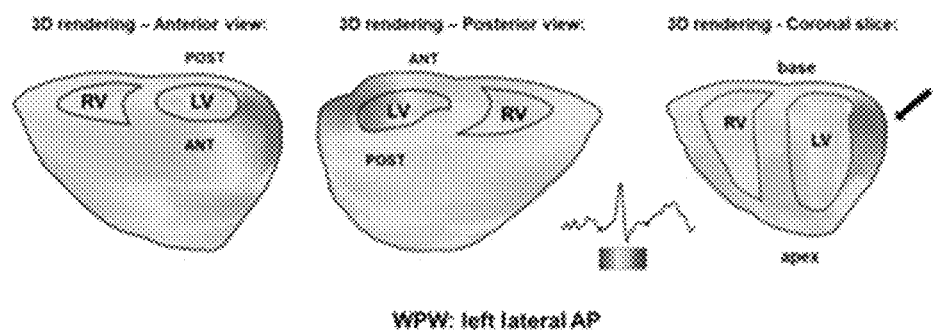
Figure 15C:
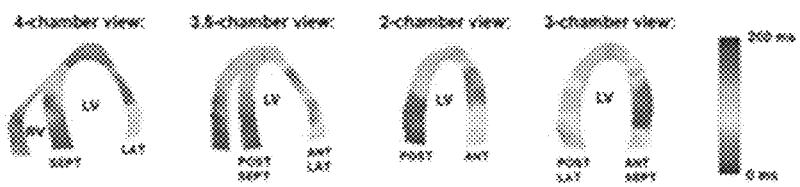
FIGS. 15C and 15D are 2D, and 3D rendered isochrone maps of a heart in a patient with Pre-Ventricular Contraction (PVC). The earliest activation time after QRS onset is 0 ms, and the latest activation time after QRS onset is 200 ms. The black arrow points at the earliest site of activation for each case. RV/LV: right/left ventricle, RA/LA: right/left atrium, Au: aorta, LAT: lateral, SEP: septum, ANT: anterior, POST: posterior.
Figure 15D:
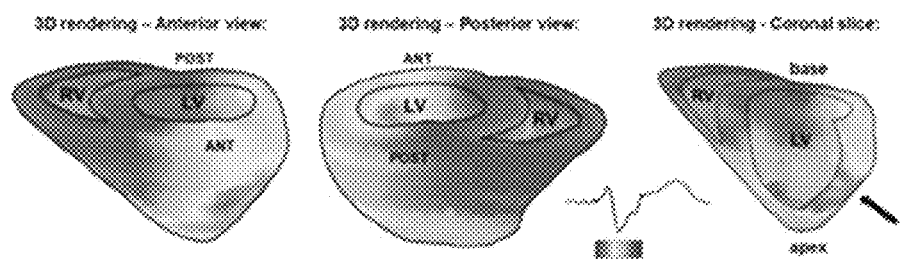

The feasibility of noninvasive 4D activation mapping of the human heart in a single heartbeat using EWI was performed in a healthy volunteer during normal sinus rhythm. Increased volume-rate ultrasound imaging was performed transthoracically and the ECG was acquired simultaneously. Snapshots of LV axial strain show early contraction in the anterior- and posterior-septal regions at the basal level after the onset of the QRS complex (FIG. 14a). Then, the electromechanical wave propagated towards the anterior and lateral region of the LV at the mid- and basal level (FIGS. 14b and 14c) and finally headed to the apex (FIGS. 12d and 12e). The electromechanical activation map (FIG. 140) illustrates the base to apex propagation, which is consistent with what was observed in the aforementioned canine case during normal sinus rhythm and in silico case.

Discussion

Cardiac arrhythmia can be associated with a life-threatening disease. Current methods used in the clinic to characterize cardiac arrhythmia are either not sufficiently spatially accurate, such as ECG, or invasive, superficial and time-consuming, such as electroanatomical mapping. A noninvasive 4D method to map cardiac activation of the full heart in all cardiac chambers can prove pivotal in the efficiency of cardiac arrhythmia diagnosis and treatment monitoring. 4D EWI is an imaging modality that not only can image the full heart noninvasively, but also is radiation-free and cost-effective.

The electromechanical activation of the entire heart can be mapped in 4D, noninvasively, and during a single cardiac cycle. The disclosed technique can be distinguished from another noninvasive method Electrocardiographic imaging which, inferring epicardial potentials from body-surface potentials, is constrained to the epicardial surface and requires wearable electrode vests as well as constructing individualized torso/heart geometries from computed tomography (CT) scans. 4D EWI can be performed with transthoracic echocardiography, and therefore its implementation on a clinical ultrasound system is appropriate. It requires using diverging wave imaging as opposed to focused beams in order to image the full heart with an increased volume-rate (≥500 volumes per second). The clinical application of this technique includes cardiac ablation treatment of arrhythmia and cardiac resynchronization therapy (CRT) for heart failure. So far, locating arrhythmia is performed invasively, using single-electrode mapping catheters under fluoroscopic guidance in the clinic involving lengthy, ionizing procedures. The use of 4D EWI can decrease the procedure time as well as the risk of complications. Regarding heart failure, up to 30%-50% of patients are reported to be non-responders to CRT while CRT response strongly depends on lead placement, which is insufficiently guided. 4D EWI can be used to optimize lead placement in CRT patients by monitoring the electromechanical activation of both ventricles simultaneously. Mapping techniques presented herein are supported by computational modeling of a realistic electromechanical human heart model for both infarct-free and infarcted hearts, which can be used to assess sudden cardiac death in post-infarction patients.

The electromechanical wave corresponds to the propagation of local myocardial shortening resulting from local electrical activation. As such, it is not a direct measurement of the electrical activity of the heart. There is a delay between the electrical and the electromechanical activation in the order of tens of milliseconds, referred as to the electromechanical delay. This delay increases from early to late sites of activations. Given that it is not feasible to acquire 3D or transmural electrical activation throughout the heart, electromechanical activation maps can serve as a reliable surrogate for electrical activation times, simultaneously informing on both the mechanical and electrical activity of the heart. This technique can be employed as a routine tool for unprecedented screening as well as for diagnosis and therapy guidelines for heart disease patients at the point of care.

Example III: Localization of Accessory Pathways in Pediatric Patients with Wolff-Parkinson-White Syndrome Using 3D-Rendered Electromechanical Wave Imaging This Example illustrates the use of the disclosed technique for prediction of the AP locations in patients.

Accessory pathways (AP) in Wolff-Parkinson-White (WPW) syndrome can be treated with catheter ablation. Localization of the AP prior to catheter ablation can be performed for pre-procedure planning. EWI can be a non-invasive and non-ionizing ultrasound-based modality that maps the electromechanical activation in all cardiac chambers at a high frame rate. In this example, EWI is used in a pediatric population. This example also shows the feasibility of using this transthoracic ultrasound technique for the localization of accessory pathways in pediatric patients with WPW.

Figure 16A:
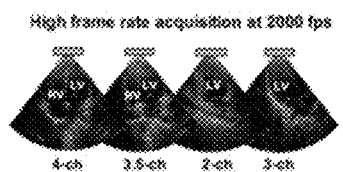
FIGS. 16A-G are a diagram illustrating exemplary stages in a method in accordance with the disclosed matter.
Figure 16B:
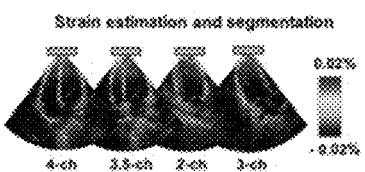
Figure 16C:
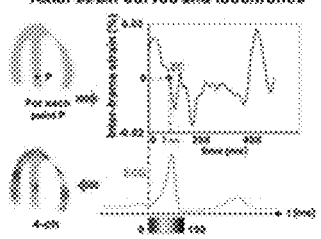
Figure 16D:
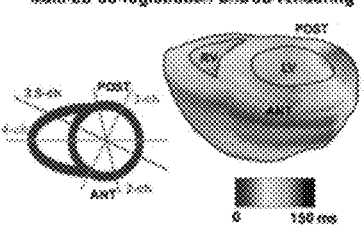
Figure 16E:
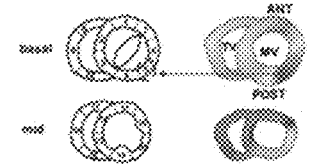

All patients underwent EWI with a trained sonographer using standard transthoracic echocardiography immediately prior to the catheter ablation procedure. Full view of the ventricular myocardium was required for EWI processing; when the anatomy was not completely visible during the initial scan, the patient was excluded from the analysis. Obtaining an EWI scan required approximately 15 minutes in the pre-operative area on the day of the procedure. The processing of each EWI scan took approximately 90 minutes, including the generation of both 2D and 3D-rendered isochrones (approximately 70 minutes for 2D only). After commencement, the protocol was amended to include an additional EWI scan immediately after the catheter ablation procedure. After generation of the EWI isochrones, a location was assigned based on a standardized segmented template of the ventricles. This template was created prior to the enrollment of patients based on similar templates in the literature with the addition of RV segments. This template includes 19 different segments (the basal segmentation is similar to standard ECG algorithms with 10 segments at the level of the AV rings as shown in FIG. 16E.

Figure 16F:
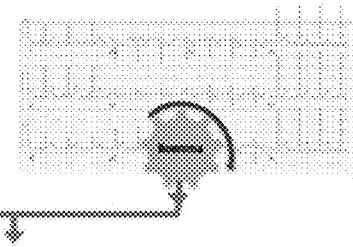
Figure 16G:
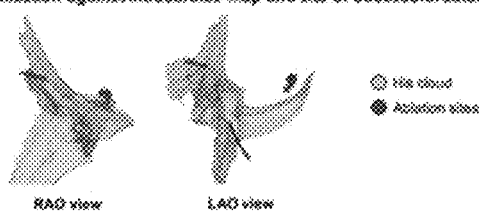

Both EWI and the clinical electrophysiologists reading the ECGs were blinded to pre-procedure planning and the outcome of the electrophysiology and ablation. The predicted AP locations based on the isochrones and on ECG were then compared to the site of successful ablation or the earliest site of activation if no ablation was attempted (FIGS. 16E-G). When computing the localization accuracy, predictions for both EWI and clinician interpretation of ECG were considered correct if they were in the same segment, or an adjacent segment, to the actual location of the AP.

Electromechanical Wave Imaging:

EWI is based on a high frame rate echocardiography sequence that transmits a single diverging wave at 2000 frames per second (fps), while simultaneously recording a Lead II ECG in synchrony with the ultrasound acquisition. The full methods pipeline is detailed in FIG. 16A-D. FIG. 16A shows 2D apical views of the heart acquired at a high frame rate of 2000 frames/second with a diverging ultrasound transmit sequence. FIG. 16B shows axial displacements and strains estimated on the radiofrequency data and the myocardium manually segmented on the first B-mode image. FIG. 16C shows the zero-crossing (ZC) locations corresponding to the activation times (t act) for each point selected on the incremental strain curves to generate the 2D isochrones. The four multi-2D electromechanical activation maps are then co-registered, and interpolation performed around the circumference to generate the 3D-rendered isochrones, displaying the earliest activation after QRS onset in red and latest in blue (FIG. 16D). A 19-segment template of the ventricles is used to predict the pathway location based on EWI results (10 segments around the atrioventricular rings include: anteroseptal, posteroseptal, left posterior, left posterolateral, left lateral, left anterolateral, left anterior, right anterior, right lateral, and right posterior).

On the right-hand side, the three corresponding cross-section slices of the 3D-rendered isochrone are displayed, with the earliest activated region visible posterolaterally at the valve level. TV: Tricuspid Valve and MV: Mitral Valve (FIG. 16E). The publicly available algorithm is performed on the 12-lead ECG to determine the AP location (FIG. 16F). Both EWI and ECG location predictions are validated against the intracardiac map and site of successful ablation (FIG. 16G). Four transthoracic apical two-dimensional views were acquired (FIG. 16A) with a 2.5 MHz phased array transducer (P4-2 ATL/Philips, Andover, Mass., USA) connected to a Vantage Research scanner system (Verasonics Inc., Kirkland, Wash., USA). A 90° and 14-cm deep field of view was used to image the ventricles. However, for adolescents older than 16 years old, it was necessary to perform the scans with larger 20-cm depth, standardly used in adults, in order to cover the entire region of interest.

Manual segmentation of the myocardium was performed on the first B-mode frame for each view and tracked automatically throughout the rest of the cardiac cycle (FIG. 16B). Motion estimation was performed axially on the radiofrequency (RF) data with 1D cross-correlation tracking. The incremental axial strains were then derived with a least-squares estimator and overlaid onto the B-mode images. The ventricular activation times were defined as the zero-crossing of the strain curves, i.e. the timing of the first change in inter-frame electromechanical axial strain after the QRS onset. The zero-crossing locations were picked for approximately one hundred randomly selected points in the segmented myocardial region of interest (FIG. 16C), and the activation times were then interpolated throughout the entire mask to achieve a homogeneous pattern. All 2D isochrones display the electromechanical activation in milliseconds, with the earliest activated region in red and the latest in blue. The four resulting multi-2D electromechanical activation maps were later co-registered around the left ventricle longitudinal axis of symmetry. In each longitudinal slice, a linear interpolation was performed around the circumference to subsequently generate the 3D-rendered isochrones (FIG. 16D).

Electrophysiology and Ablation Procedures:

All catheter ablation procedures were performed under general anesthesia using standard techniques, equipment, and electroanatomic mapping. All patients had a surface ECG recorded, followed by vascular access. After vascular access was obtained, catheters were placed near the His Bundle, right atrial appendage, right ventricular apex, and coronary sinus. Pacing protocols were performed with rapid atrial pacing from the high right atrium, atrial and ventricular extra-stimulus testing at baseline and on isoproterenol. For left-sided APs, access was obtained via trans-septal puncture. Ablation was performed with radiofrequency or cryoablation technique. AP location was determined by the site of successful ablation.

Statistical Analysis:

Data were reported as a frequency (%), median (Interquartile Range), or mean±standard deviation as appropriate. Comparisons of EWI and ECG predictions to electrophysiology and ablation results are shown on correlation maps. Heat maps of the correlation tables were generated using GraphPad Prism (version 7.03 for Windows, GraphPad Software, La Jolla Calif. USA). EWI and ECG localization performances were also quantified with general accuracy and segment-specific precision and recall analysis.

Results:

Pediatric patients with ventricular pre-excitation on 12-lead ECG have consented. All 15 patients underwent transthoracic imaging with a trained sonographer. One patient was excluded for the inability to image the entire ventricular myocardium due to a poor acoustic window. The mean age of the cohort was 13.8±2.8 years, and 50% were male. Baseline characteristics of the patients are shown in Table 1. Six patients also underwent EWI scans after their catheter ablation procedures.

TABLE 1

Patient Characteristics

| | N = 14 |
|---|---|
| Male | 7 (50.0%) |
| Age (mean) | 13.8 ± 2.8 years |
| On Antiarrhythmic Medication during EWI | 0 (0.0%) |
| Height (mean) | 158.5 ± 16.8 cm |
| Weight (mean) | 60.8 ± 24.0 kg |
| Body Surface Area (mean) | 1.63 ± 0.4 $m^2$ |
| Baseline Intervals | |
| PR (mean) | 97.4 ± 19.0 ms |
| QRS (mean) | 115.6 ± 19.4 ms |
| AH (mean) | 63.1 ± 14.5 ms |
| HV (mean) | 11.8 ± 8.9 ms |

Accessory Pathways:

Catheter mapping and ablation demonstrated a single AP in all 14 included patients. Specific locations based on a template in FIG. 16E) included 3 left lateral, 2 left posterolateral, 5 posteroseptal, 1 anteroseptal, 1 right posterolateral, 1 right anterior, and 1 fasciculoventricular pathway with the earliest ventricular activation in the mid-septal RV. The identified fasciculoventricular pathway was not ablated. Of the 13 patients for whom ablation was attempted, all 13 APs (100%) were ablated. The patient with the anteroseptal pathway was initially not ablated secondary to mechanical disruption of the pathway preventing accurate intracardiac mapping. The patient subsequently returned to the laboratory and was ablated on the second attempt. Ablation was performed with radiofrequency current in 12 patients and with cryoablation technique in 1 patient. Trans-septal puncture was performed on six patients. Median fluoroscopy time was 0.3 (0.1-3.5) minutes, and the dose of radiation was 13.2 (7.0-70.0)μ$Gym^2$, and one patient underwent ablation without fluoroscopy. The means and ranges of PR, QRS, AH, and HV intervals as determined by baseline measurements in the electrophysiology laboratory are also described in Table 1.

Electromechanical Wave Imaging and ECG predictions:

EWI predicted 14/14 (100%) of the AP locations by correctly localizing the areas of earliest ventricular activation using the segments described in the methods above. Examples of EWI isochrones are shown in the following figures: left lateral AP before and after ablation in FIG. 17, right posterolateral AP before and after ablation in FIG. 18, a posteroseptal AP before ablation in FIG. 19, and a fasciculoventricular AP in FIG. 20.

Referring to FIG. 17, baseline intervals in the electrophysiology showed PR: 75 ms QRS: 93 ms AH: 61 ms HV: 1 ms. For all isochrones, red indicates earliest activation and blue indicates latest. Four 2D EWI isochrones of the ventricles prior to catheter ablation showing earliest area of activation in the lateral LV (FIG. 17A). 2 cm scale bars are shown for spatial resolution, and a single-lead ECG obtained with EWI acquisition is included. The anterior view of the 3D-rendered EWI isochrone prior to catheter ablation and color bar for activation timings are shown in FIG. 17B.

The LAO cross-section of the previous 3D-rendered EWI isochrone at the valve level (TV: Tricuspid Valve, MV: Mitral Valve) is shown in FIG. 17C. FIG. 17D shows an electroanatomic map in LAO view showing superior vena cava (SVC), right atrium (RA), coronary sinus (CS), His site (yellow dot), and the site of successful ablation in the lateral LV (red dot). FIG. 17E shows 12-lead ECG prior to catheter ablation. FIG. 17F shows four 2D EWI isochrones of the ventricles after catheter ablation showing earliest area of activation in the septum. FIG. 17G shows the anterior view of the 3D-rendered EWI isochrone after catheter ablation showing normal sinus activation of the ventricles and color bar for activation timings. FIG. 17H shows the LAO cross-section of the 3D-rendered EWI isochrone at the valve level after catheter ablation. FIG. 17I shows a 12-lead ECG obtained after successful catheter ablation.

Figure 18D:
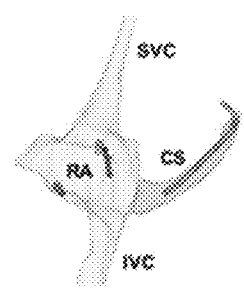

Referring to FIG. 18, baseline intervals in the electrophysiology showed PR: 75 ms QRS: 93 ms AH: 61 ms HV: 1 ms. For all isochrones, red indicates earliest activation and blue indicates latest. Four 2D EWI isochrones of the ventricles prior to catheter ablation show earliest area of activation in the lateral LV (FIG. 18A). 2 cm scale bars shown for spatial resolution and single-lead ECG obtained with EWI acquisition are again included. FIG. 18B shows the anterior view of the 3D-rendered EWI isochrone prior to catheter ablation and color bar for activation timings. FIG. 18C shows the LAO cross-section of the previous 3D-rendered EWI isochrone at the valve level (TV: Tricuspid Valve, MV: Mitral Valve). FIG. 18D shows an electroanatomic map in LAO view showing superior vena cava (SVC), right atrium (RA), coronary sinus (CS), His site (yellow dot), and the site of successful ablation in the lateral LV (red dot). FIG. 18E shows a 12-lead ECG prior to catheter ablation. FIG. 18F shows four 2D EWI isochrones of the ventricles after catheter ablation showing earliest area of activation in the septum. FIG. 18G shows the anterior view of the 3D-rendered EWI isochrone after catheter ablation showing normal sinus activation of the ventricles and color bar for activation timings. FIG. 18H shows the LAO cross-section of the 3D-rendered EWI isochrone at the valve level after catheter ablation. FIG. 18I shows a 12-lead ECG obtained after successful catheter ablation.

Referring to FIG. 19, baseline intervals in the electrophysiology showed PR: 93 ms QRS: 143 ms AH: 60 ms HV: 8 ms. For all isochrones, red indicates the earliest activation, and blue indicates latest. FIG. 19A shows the anterior view of the 3D-rendered EWI isochrone prior to catheter ablation showing earliest activation in the right posteroseptal area. The 1-lead ECG obtained with EWI acquisition is included, as well as 2 cm scale bars for spatial resolution. FIG. 19B shows the LAO cross-section of the previous 3D-rendered EWI isochrones at the valve level (TV: Tricuspid Valve, MV: Mitral Valve) and color bar for activation timings. FIG. 19C shows an electroanatomic map in LAO view showing superior vena cava (SVC), right atrium (RA), inferior vena cava (IVC), Coronary Sinus (CS), His cloud (yellow dots), and the site of successful ablation in the posteroseptal RA (red dot). FIG. 18D shows 12-lead ECG prior to catheter ablation.

Referring to FIG. 20, baseline intervals in the electrophysiology showed PR: 121 ms QRS: 93 ms AH: 70 ms HV: 15 ms. For all isochrones, red indicates earliest activation and blue indicates latest. FIG. 20A shows the anterior view of the 3D-rendered EWI isochrone prior to catheter ablation. No definitive area of earliest activation can be identified. 2 cm scale bars for spatial resolution and 1-lead ECG obtained with EWI acquisition are again included. FIG. 20B shows a coronal slice of the previous 3D-rendered isochrone. The earliest activation is seen in the mid septal RV, and A color bar for activation timings is included. The small gap in the LV apex results from a small sector of myocardium that was unable to be imaged in the 2D 3-chamber view, and therefore could not be used during the 3D interpolation as described in the methods. FIG. 20C shows a cross-section of the 3D-rendered isochrone at the level of the mid ventricles. The black dashed line displayed on the coronal slice corresponds to the exact level of the cross-section. FIG. 20D shows a 12-lead ECG acquired prior to catheter ablation.

ECG analysis correctly predicted 11/14 (78.6%) of the AP locations using the disclosed algorithms (predictions in immediately adjacent segments were considered correct). Correlation heat maps of AP location prediction with EWI vs. ECG are shown in FIG. 21. More quantitatively, precision and recall analysis is provided in Table 2 for each ventricular segment and quantifies the AP localization performances of EWI versus other ECG algorithms.

FIG. 21 shows correlation heat maps illustrating the accuracy of EWI and clinician interpretation of ECG for localization of the imaged APs (includes 10 AV ring segments as well as the location of fasciculoventricular). FIG. 21A shows AP locations from catheter mapping (columns) compared with EWI isochrone AP location predictions (rows). FIG. 21B shows intracardiac localization of APs (columns) compared with AP location predictions by publicly available algorithm (rows). FIG. 21C shows intracardiac localization of APs (columns) compared with AP location predictions by certain publicly available algorithms (rows). Green represents perfect predictions, while yellow illustrates predictions in adjacent segments, and red displays wrong predictions. The numbers written in the cells correspond to the number of predicted AP for each ventricular segment. EWI correctly predicted 100% of the AP locations. When considering adjacent segments as correct predictions, the Boersma et al. and Arruda et al. algorithms correctly predicted 78.6% of the AP locations, while when being conservative (excluding yellow cells), only 50% and respectively 57.1% of the predictions were correct.

TABLE 2

EWI vs ECG performances for AP localization

| AP localization methods | Global accuracy | Ventricular segments | | | | | | | | | | | | | |
|---|---|---|---|---|---|---|---|---|---|---|---|---|---|---|---|
| | | ANT SEPT | | POST SEPT | | Fasciculo-ventricular | | Left LAT | | Left POST LAT | | Right LAT | | Right ANT | |
| | | P | R | P | R | P | R | P | R | P | R | P | R | P | R |
| EWI | 100% | 1 | 1 | 1 | 1 | 1 | 1 | 1 | 1 | 1 | 1 | 1 | 1 | 1 | 1 |
| Boersma | 50% 78.6%* | 0.25 | 1 | 1 | 0.4 | 0 | 0 | 0.75 | 1 | 0 | 0 | 0.33 | 1 | 0 | 0 |
| Arruda | 57.1% 78.6%* | 0.33 | 1 | 0.75 | 0.6 | 0 | 0 | 0.67 | 0.67 | 0 | 0 | 0.5 | 1 | 1 | 1 |

P stands for Precision, while R stands for Recall (also known as Sensitivity)
*When prediction in the immediately adjacent segment is considered correct Complications:

There were no complications during EWI scans and no major complications during catheter ablations.

Discussion:

EWI was shown to be accurate for both localizing and visualizing the earliest ventricular activation in 14/14 included patients prior to the catheter ablation procedures. The patients were selected because they were presenting for catheter ablation. EWI localization was more accurate than ECG analysis with two different algorithms in the cohort.

The safety and efficacy of WPW ablation are documented, but approximately 6% of ablations are still unsuccessful. This is variable by pathway location, from a 98% success rate for left free wall pathways to 88-89% for septal pathways. Complications from catheter ablation of APs can be rare but can still occur. In addition, the risks of WPW ablation can vary by location, such as AV block in septal pathways, complications from trans-septal puncture in left-sided ablation, and differences in fluoroscopy and anesthesia times based on pathway location. Certain less common pathways, such as the fasciculoventricular AP, do not require catheter ablation. Having knowledge of the location of the pathway can be a factor for both planning of catheter ablation and patient counseling prior to the procedure. Adding EWI to the standard 12-lead ECG has the potential to increase the accuracy of AP localization prior to catheter ablation procedures.

EWI can localize APs in a variety of locations to an approximately 1-2 cm area of the myocardium in each case (see scale bars on FIGS. 17-20). EWI succeeded with a high number of anatomic segments surrounding the atrioventricular rings, which was consistent with or greater than 12-lead ECG algorithms (10 segments at the level of the atrioventricular rings for EWI, as seen in FIG. 16E, compared to 8 for the Boersma algorithm and 10 for the Arruda algorithm). In addition, EWI was able to correctly identify the earliest area of ventricular pre-excitation from a fasciculoventricular pathway. The latter was localized distal to the AV ring in the mid-ventricular septum, and no current AP localization algorithm would predict this location. An advantage of EWI is its ability to locate pre-excitation in ventricular myocardium below the level of the atrioventricular rings. EWI also aided in localizing premature ventricular contractions in a single patient and accurately illustrating the propagation of atrial activation in normal sinus rhythm. The exact spatial resolution is dependent on both the quality of imaging and the location of the pathway and is illustrated on a case by case basis with scale bars in each figure. When using 2D echocardiography, the location of the myocardial points imaged can affect the specificity of the EWI results. For example, as seen in the methods (FIG. 16D), there are eight image samples around the left ventricle but only four in the right ventricle. This inherently means that the spatial resolution of EWI can be higher for left-sided accessory pathways. Nevertheless, EWI can localize all pathways regardless of location, assuming proper quality echocardiography.

The degree of pre-excitation did not affect the accuracy of EWI in this cohort. While most patients were substantially pre-excited (as described in Table 1), the presence of less obvious pre-excitation did not affect the resulting localization. For example, one patient with a left posterolateral pathway (Baseline Intervals: PR: 118 ms QRS: 103 ms AH: 46 HV: 28) was imaged and localized with EWI, suggesting use of EWI in patients with minimal pre-excitation.

EWI can consistently localizing accessory pathways in variable locations more frequently than the 12-lead ECG in a pediatric patient population. A higher correlation was obtained between the electroanatomic mapping results and EWI predictions than against ECG predictions. EWI isochrones can also provide more detailed anatomical visualization. These findings indicate that this modality has the potential to better inform a treating electrophysiologist for pre-procedure planning.

Example IV: Non-invasive Localization of Cardiac Arrhythmias Using Electromechanical Wave Imaging This Example illustrates the use of the disclosed techniques for non-invasive localization of cardiac arrhythmias using electromechanical wave imaging.

Cardiac arrhythmias can be a cause of morbidity and mortality which can require invasive catheter ablation for the curative treatment. Diagnosis and localization of arrhythmias can be used for clinical decision making and treatment planning. During invasive electrophysiology (EPS), extensive operating room time can be required to build anatomical activation maps of the heart during the arrhythmia. Arrhythmias on the left side of the heart can require trans-septal puncture and therapeutic systemic anticoagulation to prevent clot formation and arterial embolism. EWI was used in this example for localization of cardiac arrhythmias such as WPW syndrome, PVC, AT and AFL.

Electrocardiogram (ECG) algorithms can be used to aid in localization. Certain algorithms for localizing APs and focal ATs can have accuracies of up to 90-93%, while localization of ectopic ventricular rhythms can be between 72-82%. However, the accuracy of these ECG algorithms can be lower in real-world clinical practice. EWI can facilitate pre-procedural discussions with patients, preoperative planning, and reduce procedural catheter mapping times.

EWI can be an ultrasound technique that can map the electromechanical wave corresponding to the propagation of the contraction onset in response to the heart's electrical activation. Unlike mechanical strain-based techniques such as Tissue Doppler Imaging (TDI) and Speckle Tracking Echocardiography (STE), EWI can be based on incremental strains. The latter is able to detect contractions on the order of 0.01%, while certain TDI techniques use global accumulated strains of approximately 30% throughout systole. In addition, TDI can be an angle dependent technique, whereas EWI activation maps can be angle independent. STE can estimate displacements in any direction by tracking the movement of speckle patterns from frame to frame at lower frame rates than EWI and can be less accurate than time-shifted based techniques such as radiofrequency-based (RF) cross-correlation. One challenge for producing accurate electromechanical activation maps can be the brief length of the electrical activation. Since ventricular depolarization occurs within 50-60 milliseconds, mapping requires a resolution of a few milliseconds (ms). Therefore, high frame rate ultrasound sequences, in this case up to 2000 Hz, can be required. Furthermore, EWI processing can rely on RF signals in order to estimate displacements in the time domain.

EWI isochrones can characterize electromechanical activation patterns of normal sinus rhythm and pacing in a reproducible, view independent and angle-independent manner. The isochrone generation process can be independent of patient geometry, and anatomical assumption of longitudinal symmetry can be reduced when rendering the activation maps. EWI can also be used to differentiate epicardial from endocardial ventricular origins in focally paced canine ventricles. Certain echocardiography strain-based methods have been investigated for identification of arrhythmia such as AP localization.

Since EWI can be an ultrasound-based technique, it is portable and there is readily available infrastructure in hospitals and clinics for potential implementation. In addition, ultrasound can be cost-effective imaging modality. Other non-invasive electrical mapping approaches such as electrocardiographic imaging (ECGI) provide high spatial resolution maps of arrhythmias, however they require computed tomography (CT) or magnetic resonance imaging (MRI), which can be ionizing or time-consuming, to obtain the patient's cardiac geometry. ECGI can be applied to the epicardial surface, however endocardial mapping can be a challenge, as can the inverse solution in ECGI.

The disclosed techniques can be used to determine the clinical accuracy of transthoracic EWI for non-invasively localizing clinical arrhythmias including WPW, PVC, AT, and AFL in adults by utilizing 3D-rendered EWI maps in all four chambers of the heart. The diagnostic accuracy of both atrial and ventricular EWI isochrones, multi-2D or 3D-rendered, with 12-lead ECG based localization was compared by expert electrophysiologists, a well-known technique using 3D electroanatomical maps performed with invasive catheter mapping and eventual successful site of ablation.

Materials and Methods

Double-Blinded Clinical Study Design

EWI was performed in patients who presented with WPW, PVC, AT and AFL for catheter ablation. Patient characteristics were obtained from preoperative histories and medical records (Tables 3 and 4).

TABLE 3

| Patient Characteristics | |
|---|---|
| | N = 55 |
| Characteristic: | |
| Male | 39 (71%) |
| Age (mean) | 56.0 ± 2.3 years |
| Diagnosis | |
| WPW | 12 (22%) |
| PVCs | 11 (20%) |
| AT | 7 (13%) |
| AFL | 25 (45%) |
| Comorbidities | |
| CAD | 8 (15%) |
| CKD | 3 (5%) |
| CHF | 18 (33%) |
| Stroke or TIA | 8 (15%) |
| Atrial Fibrillation | 14 (25%) |
| VTA/F | 4 (7%) |
| Previous Catheter Ablation | 7 (13%) |
| Previous Cardiac Surgery | 9 (16%) |
| On Antiarrhythmic Medication | 14 (25%) |
| Previous Echocardiography data | N = 40 |
| LVEF (mean) | 45.4 ± 2.6% |
| LVEF < 50% | 17 (42.5%) |
| LA Diameter (mean) | 3.9 ± 0.8 cm |
| LA Diameter ≥ 4.0 cm | 15 (37.5%) |
| LVEDD (mean) | 5.2 ± 0.1 cm |
| Wall motion abnormality | 7 (18%) |
| History of Limited Echo* | 8 (20%) |
| Body Surface Area (mean) | 2.0 ± 0.1 m$^2$ |
| WPW patients | N = 12 |
| QRS duration (mean) | 127 ± 3 ms |
| PVC Patients | N = 11 |
| PVC burden (mean) | 29 ± 2% |
| AFL Patients | N = 25 |
| Cycle Length of AFL (mean) | 270 ± 6 ms |
| AT Patients | N = 7 |
| Cycle Length of focal AT (mean) | 362 ± 20 ms |

TABLE 4

| Patient Characteristics by Subgroup | | | | | |
|---|---|---|---|---|---|
| Comorbidities | WPW | PVC | AFL | AT | Total |
| CAD | 1 (8%) | 1 (9%) | 5 (20%) | 1 (14%) | 8 (15%) |
| CKD | 1 (8%) | 0 (0%) | 2 (8%) | 0 (0%) | 3 (5%) |
| CHF | 0 (0%) | 7 (64%) | 10 (40%) | 1 (14%) | 18 (33%) |
| Stroke or TIA | 0 (0%) | 1 (9%) | 5 (20%) | 2 (29%) | 8 (15%) |
| Atrial Fibrillation | 2 (17%) | 0 (0%) | 9 (36%) | 3 (43%) | 14 (25%) |
| VTA/F | 0 (0%) | 0 (0%) | 4 (16%) | 0 (0%) | 4 (7%) |
| Previous Catheter Ablation | 1 (8%) | 1 (9%) | 3 (12%) | 2 (29%) | 7 (13%) |
| Previous Cardiac Surgery | 1 (8%) | 0 (0%) | 5 (20%) | 3 (43%) | 9 (16%) |

TABLE 4-continued

Patient Characteristics by Subgroup

| Comorbidities | WPW | PVC | AFL | AT | Total |
|---|---|---|---|---|---|
| On Antiarrhythmic Medication | 1 (8%) | 0 (0%) | 8 (32%) | 5 (71%) | 14 (25%) |
| Previous Echocardiography data | N = 6 | N = 11 | N = 17 | N = 6 | N = 40 |
| LVEF (mean) | 57 ± 6 | 39 ± 18 | 43 ± 17 | 55 ± 19 | 45.4 ± 2.6% |
| EF < 50% | 0 (0%) | 7 (64%) | 9 (36%) | 1 (14%) | 17 (42.5%) |
| LA Diameter (mean) | 3.0 ± 0.7 | 3.7 ± 0.5 | 4.5 ± 0.6 | 4.2 ± 0.8 | 3.9 ± 0.8 cm |
| LA ≥ 4.0 cm | 1 (8%) | 4 (36%) | 9 (36%) | 1 (14%) | 15 (37.5%) |
| LVEDD (mean) | 4.8 ± 0.4 | 5.5 ± 0.8 | 5.1 ± 0.5 | 5.0 ± 0.6 | 5.2 ± 0.1 cm |
| Wall Motion Abnormality | 0 (0%) | 5 (45%) | 2 (8%) | 0 (0%) | 7 (18%) |

All patients presenting for one of the four included arrhythmias were considered. Only during initial feasibility testing, the first thirteen patients were processed in a single-blinded manner such that the EPS operators were blinded to EWI results, but EWI was not blinded to catheter ablation results. All data from the subsequent 42 patients were processed as a double-blinded study. The trained sonographer and the engineers who processed the EWI were blinded to the 12-lead ECG prior to each patient's catheter ablation, the EPS results, and the 3D electroanatomical maps. The operating electrophysiologists were blinded to all EWI results. Six board-certified electrophysiologists not involved in the patient's care were blinded from EWI and 3D electroanatomic maps and asked to use each patient's 12-lead ECG prior to ablation to predict the arrhythmia site of origin or location of the AP. They were allowed to use any algorithm for localization.

All patients with an AP had manifest ventricular pre-excitation on their resting ECG. Patients presenting for PVC ablation had monomorphic PVCs, and those presenting for AFL or AT ablation presented in those respective rhythms during EWI. For AP and PVC locations, EWI and ECG readers used a standardized segmented map of the ventricles with 21 anatomic locations to predict the origin (FIG. 28). This map was designed prior to patient enrollment. Reads were considered correct if predictions fell in the exact segment or in a directly adjacent segment to the actual location of the arrhythmia. For AT and AFL patients, both clinicians and EWI assessed whether the arrhythmia was a typical CTI AFL, or of other right atrial versus left atrial origin (FIG. 28). FIG. 28 shows the segmented heart template of the right and left ventricles used for interpretation of EWI and ECG results in comparison with the site of successful ablation. 21 ventricular segments were delineated (including 1 each for the RVOT and LVOT not shown) and three additional atrial classification categories were used. EWI localizations for all diagnoses were determined based on the earliest activated regions on the 2D isochrones prior to 3D rendering. Results of EWI and ECG analysis were compared directly to the 3D electroanatomical maps and the site of successful ablation.

Electromechanical Wave Imaging

EWI can rely on a high frame rate ultrasound flash sequence that emits a single diverging beam at 2000 frames/second. Two-dimensional ultrasound acquisitions in four apical echocardiographic views were performed at a 20-cm depth using a Vantage Research scanner (Verasonics Inc., Kirkland, Wash., USA) with a 64-element 2.5 MHz phased array (P4-2 ATL/Philips, Andover, Mass., USA). The high frame rate radiofrequency (RF) data was acquired for 2 seconds, followed by a 1.5 second focused anatomical B-mode sequence at 30 frames/second. Lead II recordings of the ECG were obtained simultaneously by the system and synchronized with the EWI acquisitions. These ECG recordings were later used for temporal co-registration across EWI views by manually selecting the QRS and p-wave onset, for the ventricles and atria respectively. The same heartbeat morphology was selected on the separate multi-2D view ECGs in order to maintain consistent starting times across all four isochrones. The EWI RF signals were reconstructed with a standard delay and sum beamforming algorithm. Myocardial wall segmentation of the chambers of interest was performed manually on the first anatomical B-mode image and automatically tracked in all subsequent frames of the cardiac cycle through systole. The motion was estimated axially with 1D cross-correlation tracking on the RF data with a window size of 10 wavelengths and 90% overlap, followed by a least-squares strain estimator with a 5-millimeter kernel to compute the electromechanical axial strain.

The quality of echocardiogram imaging can be dependent on the skills of the operator. However, the EWI isochrone generation process can be independent of the patient geometry or on the skills of the technician holding the probe. The type of strain, whether axial or radial, is of no consequence as the only important factor is the sign change of the strain. For computational efficiency, activation times were manually selected on the incremental strain curves for a subset of approximately one hundred points, randomly and automatically chosen by downsampling the total number of pixels contained in the segmented mask. Activation times (tact) were defined as the timing of the first change in inter-frame or incremental axial strain from relaxation to contraction (also known as zero-crossing (ZC) after the QRS and the p-wave onset, for the ventricles and atria respectively). During active contraction that follows isovolumic contraction, a change from lengthening to shortening in the axial direction of the myocardium is detected. Therefore, this corresponds to a positive-to-negative downward ZC (shortening) in the apical views, as the myocardium walls are mostly aligned with the ultrasound beam during contraction with the exception of the atrial roof. In that case, since the wall is orthogonal to the beam's direction, the activation times correspond to the negative-to-positive upward ZC (thickening). A Delaunay triangulation-based cubic interpolation was then applied to the scattered activation time values to achieve a homogeneous isochrone pattern throughout the entire myocardium mask grid. The four resulting 2D isochrones or activation maps display the activation time (in milliseconds) from the point of interest (onset of p-wave or QRS) with earliest activation displayed in red and latest in blue.

After obtaining the multi-2D isochrones in the four apical standard views, the left ventricle median axis or longitudinal apex to the base rotation axis of the probe (dotted black lines in FIG. 27) was automatically detected on each view. Relative positions of the four 2D imaging planes were assumed to be organized as in the theoretical case with pre-set probe rotation angles: 60° clockwise between the 4-ch and 2-ch, 30° clockwise between the 4-ch and 3.5-ch, and finally 60° counter-clockwise between the 4-ch and 3-ch view. The four 2D isochrone slices were then automatically co-registered spatially around the LV longitudinal axis of rotation and a linear interpolation of the activation times was performed around the circumference.

Figure 35A:
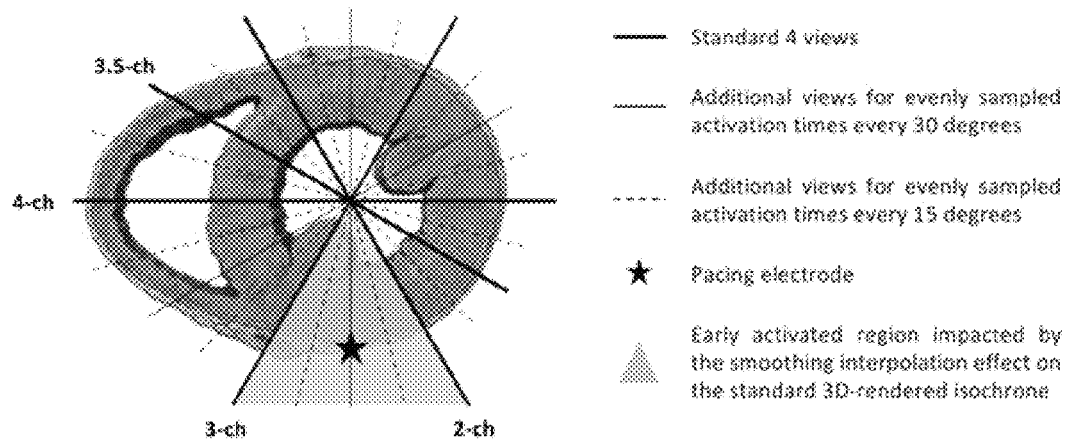
FIGS. 35A-B are diagrams illustrating multi-2D sampling effects on the resolution of 3D-rendered EWI in an open-chest canine with a single LV pacing location.

The impact of multi-2D sampling on the spatial resolution of 3D-rendered EWI was tested by performing two open-chest procedures on LV paced canines. For the first the canine's LV was paced at 5 different locations, and the usual four EWI apical views were acquired each time by the sonographer (FIG. 34), while for the second dog the LV was paced at a single location, but additional apical multi-2D views were acquired (FIG. 35). A robotic arm was used in the latter to accurately measure the rotation angle of the probe between the additional EWI planes: either 6 evenly spaced slices by 30-degree angles or 12 evenly spaced slices by 15-degree angles (FIG. 35A).

Figure 27:
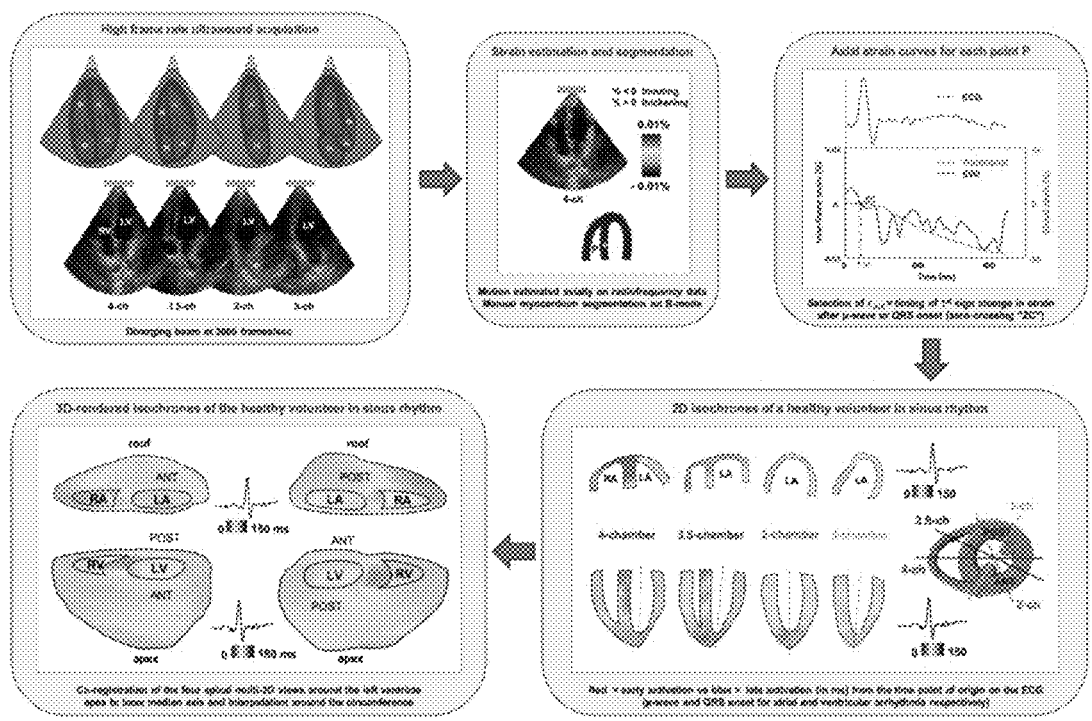
FIG. 27 is a diagram illustrating an exemplary EWI workflow in accordance with the disclosed matter.

3D-rendering of the EWI maps were generated. The 3D-rendering algorithm runs in MATLAB, outputs the 3D-rendered isochrones as 3D arrays and the volumes were then imported into Amira for better visualization and manipulation. On top of static images, more dynamic visualization was achieved by playing the isochrones over time, enabling better characterization of macro-reentrant circuits. The workflow of the entire EWI processing pipeline is shown in FIG. 27. Obtaining an EWI scan with the four multi-2D views took approximately 15 minutes in the pre-operative area on the day of the procedure, while the off-line processing of each EWI scan required approximately 90 minutes, including generation of both multi-2D and 3D-rendered isochrones (approximately 70 minutes for 2D isochrones only).

EPS and Ablation

Clinical EPS were performed using standard equipment and electroanatomic mapping (CARTO, Biosense Webster, Diamond Barr, Calif., USA or EnSite, Abbott Medical, Inc., St. Paul, Minn., USA). After obtaining vascular access, multi-electrode catheters were positioned under direct fluoroscopy. A surface ECG was recorded prior to ablation. The average procedure time in this cohort was 147±60 minutes with an average fluoroscopy time of 20.0±14.1 minutes. Entrainment maneuvers, activation sequence mapping, and electroanatomical mapping were performed for patients presenting with AFL, AT, or a conducting AP participating in a clinical arrhythmia.

For patients presenting for PVC or WPW ablation with manifest ventricular pre-excitation, the ablation site was determined by the earliest activation during electro-anatomic mapping either in the sinus or ventricularly paced rhythm.

Statistics

Data were expressed as frequency (%) or mean±standard error of the mean as appropriate. Variability analysis for ECG interpretations was performed using Light's Kappa method (48). Odds ratios for comparison of EWI to ECG were achieved using a generalized linear mixed model, except when prevented by separation, in which case exact logistic regression was used. Univariate logistic regression, chi-square tests, or Fisher's exact tests were used for univariate analysis as appropriate. Variables reaching p<0.10 in univariate analysis were included in multivariate analysis. Multivariate analysis was performed with logistic regression. Statistical analysis was performed using both SPSS statistical software (Version 24, IBM corp.) and STATA Statistics/Data Analysis (Version 15, Stata Corp.).

Results

Figure 22:
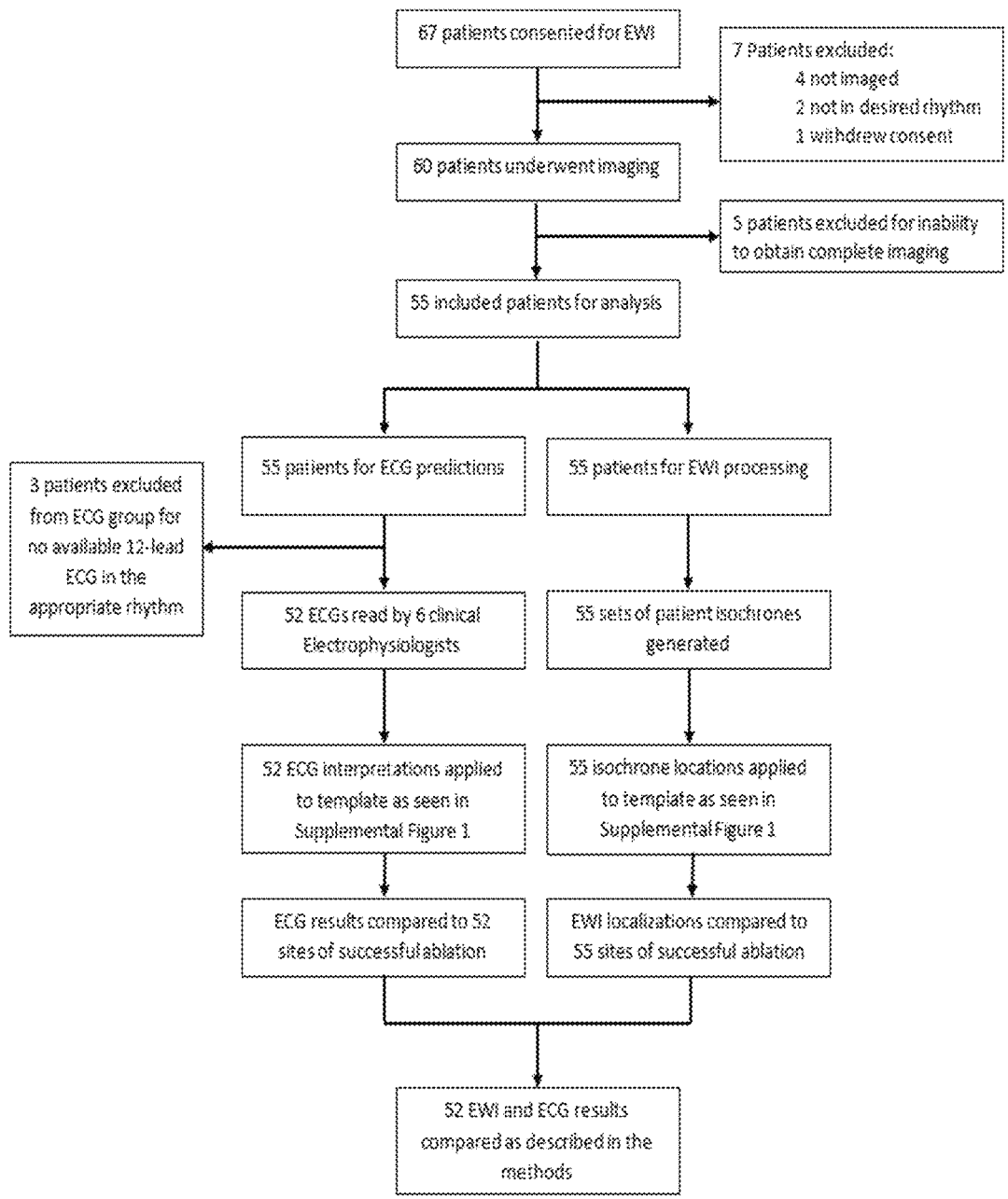
FIG. 22 is a diagram illustrating exemplary patient recruitment and indications for exclusions in accordance with the disclosed matter.

Sixty-seven patients for catheter ablation of WPW, PVC, AT and AFL, were consented for EWI. Twelve patients were excluded: 1 withdrew consent prior to imaging, 2 were not in the clinical arrhythmia as expected, and 4 were not imaged. The resulting cohort of fifty-five patients underwent EWI (FIG. 22). Examples of isochrones from WPW, PVC, AT and AFL are shown in FIG. 23. FIG. 23 shows 3D-rendered EWI isochrones of the four included arrhythmia types. Red represents the earliest activated region and blue the latest. Each case includes the 12-lead ECG prior to catheter ablation and arrow bars for scale (in cm). FIG. 23A shows EWI isochrones of a patient with WPW and a left lateral AP. FIG. 23B shows EWI isochrones of a patient with PVCs originating from the left anterior papillary muscle. Views shown (top to bottom for (23A) and (23B)) include 3D-rendered ventricular isochrone in anterior view with single-lead ECG obtained during EWI acquisition, coronal cross-section of the 3D-rendered isochrone, and transverse cross-section at the level of the valves. FIG. 23C shows EWI isochrones of a patient with a focal AT originating from the posterolateral high right atrium. FIG. 23D shows EWI isochrones of a patient with a mitral AFL. Views shown for 23C and 23D include anterior (left) and posterior (right) views of the 3D-rendered atrial isochrones with single-lead ECG obtained during EWI acquisition displayed below. The mean age was 56.0±2.3 years of age, and 71% were men. 18% (n=7) of the cases had wall motion abnormalities by conventional 2D echocardiography. Full baseline characteristics are given in Table 3 and other measurements including atrial size, decreased left ventricular ejection fraction and history of prior ablations or surgeries by subgroup in Table 4.

Accessory Pathways

Twelve patients with manifest pre-excited 12-lead ECGs were imaged with EWI prior to AP ablation. There were 3 left lateral, 1 left anterolateral, 4 posteroseptal, 1 right posterior, and 3 anteroseptal pathways. Catheter ablation was successful in 100% of cases, which was defined as loss of the delta wave on 12-lead ECG and if supraventricular tachycardia was no longer inducible. An analysis of correct predictions for EWI was performed using the segmented template described in FIG. 28. EWI correctly predicted 12/12 (100%) of the AP locations (Table 5).

Representative images of a left lateral AP including 2D and 3D isochrones are shown in FIG. 23A and representative images of a posteroseptal AP including 2D and 3D isochrones are shown in FIG. 29. FIG. 29 shows the EWI isochrones of a 34-year-old patient presenting for ablation of a posteroseptal accessory pathway. For all isochrones, red represents the earliest activated region and blue the latest. FIG. 29A shows 12-lead ECG obtained at the time of EWI acquisition prior to catheter ablation. FIG. 29B shows four 2D EWI isochrones of the ventricles illustrating the earliest point of activation in the basal posteroseptal wall and arrow bars displaying the isochrone scale (in cm). FIG. 29C shows 3D-rendered isochrones of the ventricles in the anterior view (left image) and posterior view (right image) showing earliest activation in the posteroseptal region alongside the single-lead ECG obtained during EWI acquisition. FIG. 29D shows Coronal slice of the anterior 3D-rendered isochrone. FIG. 29E shows horizontal cross-section of the 3D-rendered isochrones at the level of the basal ventricles.

TABLE 5

EWI and ECG Results a. *Overall Correct

| Diagnosis | EWI (N) | EWI % Correct | ECG (N) | ECG % Correct |
|---|---|---|---|---|
| WPW | 12 | 100 | 72 | 64 |
| PVC | 11 | 91 | 60 | 80 |
| AT | 7 | 100 | 36 | 50 |
| AFL | 25 | 96 | 144 | 74 |
| AT and AFL combined | 32 | 97 | 180 | 70 |
| Total | 55 | 96 | 312 | 71 | b. **Direct Comparison of EWI vs. 12-Lead ECG

| Diagnosis | Odds Ratio (95% CI) | p |
|---|---|---|
| WPW | 9.1 (1.4-∞) | 0.016 |
| PVC | 2.25 (0.2-23.4) | 0.497 |
| AT | 7.53 (1.0-∞) | 0.051 |
| AFL | 8.2 (1.0-67.1) | 0.049 |
| AT and AFL combined | 13.1 (1.6-104.6) | 0.015 |
| All Patients (unadjusted for diagnosis) | 11.8 (2.2-63.2) | 0.004 |
| All Patients (adjusted for diagnosis) | 12.1 (2.3-63.2) | 0.003 | c. Inter-observer Agreement of ECG reads between clinicians

| Diagnosis | Kappa (agreement)(48) |
|---|---|
| WPW | 0.33 (minimal) |
| PVC | 0.33 (minimal) |
| AT | 0.00 (none) |
| AFL | 0.37 (minimal) |
| AT and AFL combined | 0.36 (minimal) |

Premature Ventricular Complexes

Eleven patients were recruited prior to catheter ablation of PVCs and imaged with EWI. PVC locations in these patients confirmed after EPS included 4 septal right ventricular outflow tract (RVOT), 1 high posterior RVOT, 1 aorto-mitral continuity, 1 right coronary sinus of Valsalva, 1 epicardial LV summit, 1 left anterior papillary muscle, 1 posterior papillary muscle of the tricuspid valve, and 1 RV septum. The mean PVC burden was 29±2% (as determined by 24-hour Holter monitor or implanted cardiac monitor). Catheter ablation was successful, defined as absence and non-inducibility (absence with and without IV isoproterenol) of primary PVC morphology, in 10/11 (91%) cases.

An analysis of correct predictions for EWI was performed using the segmented template (FIG. 28), notably including single segments for the RVOT and left ventricular outflow tract (LVOT) respectively. EWI correctly identified 10/11 (91%) of PVC locations (Table 5). In the single case, EWI was unable to locate the PVC origin, no area of earliest activation can be determined on the isochrones. In this case, the PVCs originated from the RVOT which was outside of the acquired EWI views as transthoracic imaging of the RVOT is limited.

Representative images from the patient with left anterior papillary muscle PVCs are shown in FIGS. 23B, and 23D and 3D isochrones of both consecutive sinus and PVC beats prior to catheter ablation, are shown in FIGS. 30A-30G.

FIGS. 30A-30G show the EWI isochrones of a 65-year-old patient presenting for ablation of frequent PVCs originating from the left anterior papillary muscle.

For all isochrones red represents the earliest activated region and blue the latest. FIG. 30A shows 12-lead ECG obtained at the time of EWI acquisition prior to catheter ablation. Red boxes outline the PVC beat, while green boxes outline the sinus beat. FIG. 30B shows four 2D EWI isochrones of the ventricles during a sinus beat prior to catheter ablation and arrow bars displaying the isochrone scale (in cm). FIG. 30C shows 3D-rendered isochrones of the ventricles (anterior view) during the sinus beat alongside the single-lead ECG obtained during EWI acquisition. FIG. 30D shows coronal section of the 3D-rendered isochrone during the sinus beat. FIG. 30E shows four 2D EWI ventricular isochrones of the same patient during a consecutive PVC beat illustrating the earliest point of activation in the mid-left anterolateral ventricle and arrow bars displaying the isochrone scale (in cm). FIG. 30F shows 3D-rendered isochrones of the ventricles in PVC (anterior view) with the earliest point of activation seen in the anterolateral LV alongside the single-lead ECG obtained during EWI acquisition. FIG. 30G shows coronal section of the 3D-rendered isochrone of the PVC.

Focal Atrial Tachycardia

Seven patients presented for focal AT ablation with the following locations identified on EPS: 2 high posterior right atrium, 1 right atrial septum, 1 crista terminalis, 1 low lateral right atrium, 1 left inferior pulmonary vein, and 1 left atrial roof tachycardia originating from an accessory pulmonary vein. Therefore 5 originated from the right atrium and 2 originated from the left atrium. The mean cycle length of the ATs was 362±20 ms. Catheter ablation was successful in terminating 100% of AT cases. Analysis of correct predictions was performed as described herein. EWI identified 7/7 (100%) of the AT locations (Table 5).

Representative images of 2D isochrones and electroanatomic maps of a left atrial roof AT, as well as the four-chamber isochrone co-registered to the pre-ablation CT scan, are shown in FIG. 24. The case displayed in FIG. 24 is from a patient with previous pulmonary vein ablation who had an AT originating at the ostium of an accessory pulmonary vein in the LA roof. Representative images of 2D and 3D-rendered isochrones of a patient with posterior right atrium AT are shown in FIG. 24C and FIG. 31. FIG. 24 shows the EWI isochrones of a 64-year-old presenting for AT ablation after previous pulmonary vein isolation. On pre-ablation CT scan the patient was noted to have an accessory pulmonary vein originating from the left atrial roof. Red on the isochrones represents the earliest activated region and blue the latest. FIG. 24A shows four 2D EWI isochrones of the atria illustrating earliest activation on the left atrial roof, arrow bars displaying the scale (in cm) and single-lead ECG obtained during EWI acquisition. FIG. 24B shows CT scan of the left atrium (blue) and left ventricle (orange) alongside the electroanatomic map during the ablation procedure. On the electroanatomic map, the red arrow illustrates the initial site of ablation, when the arrhythmia was believed to be originating from the mitral area. The green arrow illustrates the successful site of ablation at the location of the accessory pulmonary vein. FIG. 24C shows 12-lead ECG obtained during EWI acquisition and prior to the EPS. FIG. 24D shows four-chamber atrial isochrone overlaid onto the full cardiac CT scan. The green arrow points to the accessory pulmonary vein and matches the location of the earliest activated region in the roof of the isochrone. Of note, transthoracic echocardiography was difficult in this patient, resulting in the 3.5- and 2-chamber views being more closely aligned than expected, and therefore preventing 3D rendering.

Figure 31A:
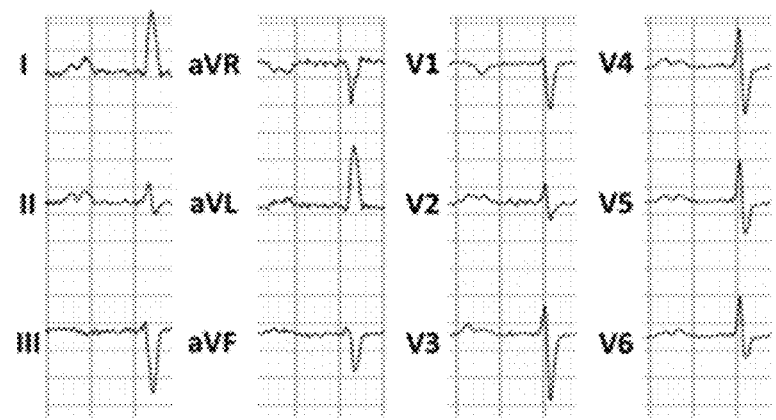
FIGS. 31A-C are example EWI isochrones of a right posterior atrial tachycardia.
Figure 31B:
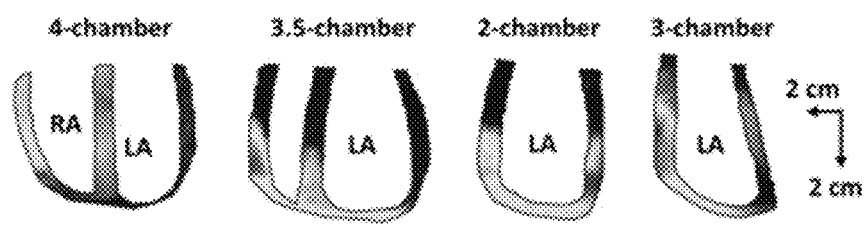
Figure 31C:
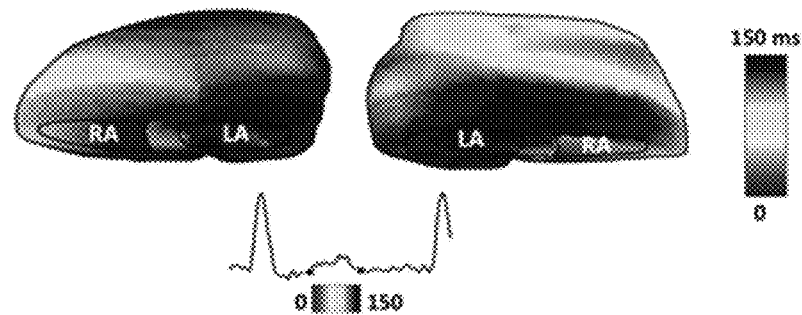

FIG. 31 shows the EWI isochrones of a 74-year-old patient presenting for ablation of an AT. For all isochrones red represents the earliest activated region and blue the latest. FIG. 31A shows 12-lead ECG obtained at the time of EWI acquisition prior to catheter ablation. FIG. 31B shows four 2D EWI isochrones of the atria with the earliest point of activation in the high right posterolateral atrium and arrow bars displaying the isochrone scale (in cm). FIG. 31C shows 3D-rendered isochrones of the atria in the anterior view (left image), and posterior view (right image) with single-lead ECG obtained during EWI acquisition displayed below.

Figure 32A:
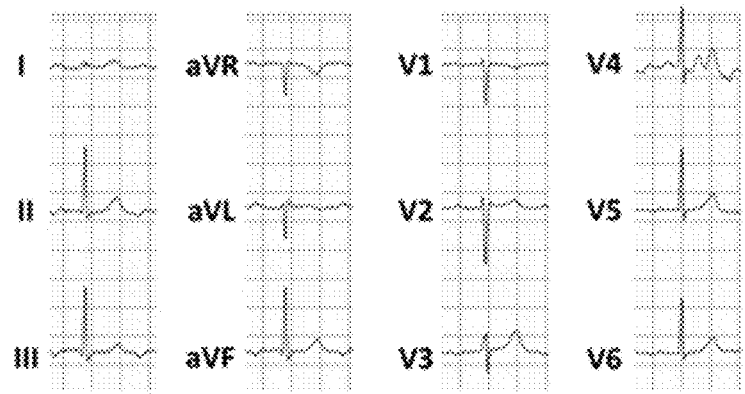
FIGS. 32A-C are example EWI isochrones of a right lateral free wall atrial tachycardia.
Figure 32B:
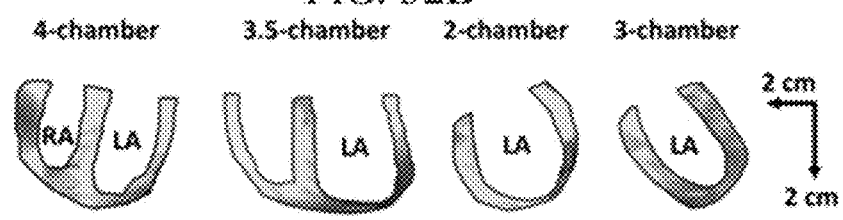
Figure 32C:
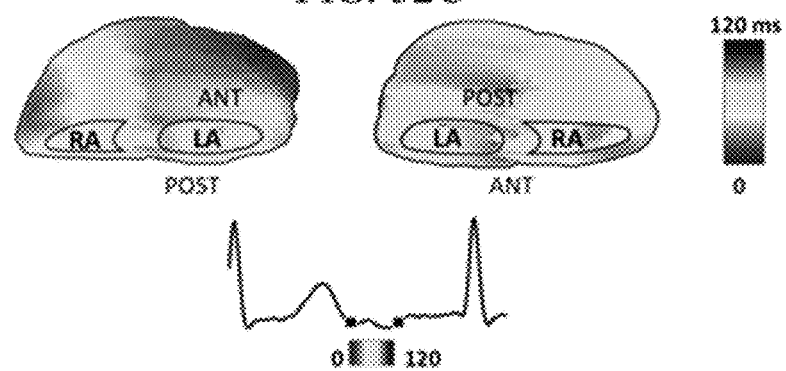

A second patient with a right atrial free wall AT is shown in FIG. 32, illustrating the difference between the earliest activation in the lateral wall (4-chamber view isochrone) vs. the posterior wall of the right atrium (3.5-chamber view isochrone), as seen in FIG. 31. FIG. 32 shows the EWI isochrones of a 34-year-old patient presenting for ablation of an AT. For all isochrones red represents the earliest activated region and blue the latest. FIG. 32A shows 12-lead ECG obtained at the time of EWI acquisition prior to catheter ablation. FIG. 32B shows four 2D EWI isochrones of the atria with the earliest point of activation in the lateral right atrium and arrow bars displaying the isochrone scale (in cm). FIG. 32C shows 3D-rendered isochrones of the atria in the anterior view (left image), and posterior view (right image) with single-lead ECG obtained during EWI acquisition displayed below.

Atrial Flutter

Twenty-five patients presented for ablation of AFL. Twenty-one had cavotricuspid isthmus dependent (CTI) dependent flutter, and 4 had atypical atrial flutters originating from the left atrium. Of the atypical flutters, 2 were mitral AFLs, 1 was a left atrial roof AFL, and 1 left atrial anterior wall AFL. Mean cycle length of the tachycardias was 270±6 ms. Catheter ablation was acutely successful in terminating 24/25 (96%) of AFL cases. EWI correctly identified the location of 24/25 (96%) of the AFL circuits (Table 5). Representative images of anterior and posterior views of multi-2D EWI isochrone slices are shown for a CTI (FIG. 25A) and a mitral AFL (FIG. 25B). Isochrones for the mitral AFL in FIG. 25B are shown over a shorter time scale in FIG. 33, allowing for better characterization of the direction of propagation. FIG. 25 shows four heat maps illustrating the EWI and ECG predictions for both (25A) WPW and (25B) PVC locations as compared to intracardiac mapping. Rows indicate EWI or ECG predictions while columns represent intracardiac mapping locations.

The numbers on each axis correspond to the location as labeled in FIG. 28. The number in each cell indicates the number of predictions in that location as predicted by EWI or ECG respectively. Green indicates an exactly correct prediction. Yellow indicates a prediction in an adjacent segment, which was counted correct in the results and as displayed in Table 5. Red indicates an incorrect prediction. There was no change in accuracy for EWI if only exact predictions were considered correct. ECG accuracy for AP localization fell from 64% to 47% while PVC localization fell from 80% to 75% if only exact segments were considered correct.

Figure 33:
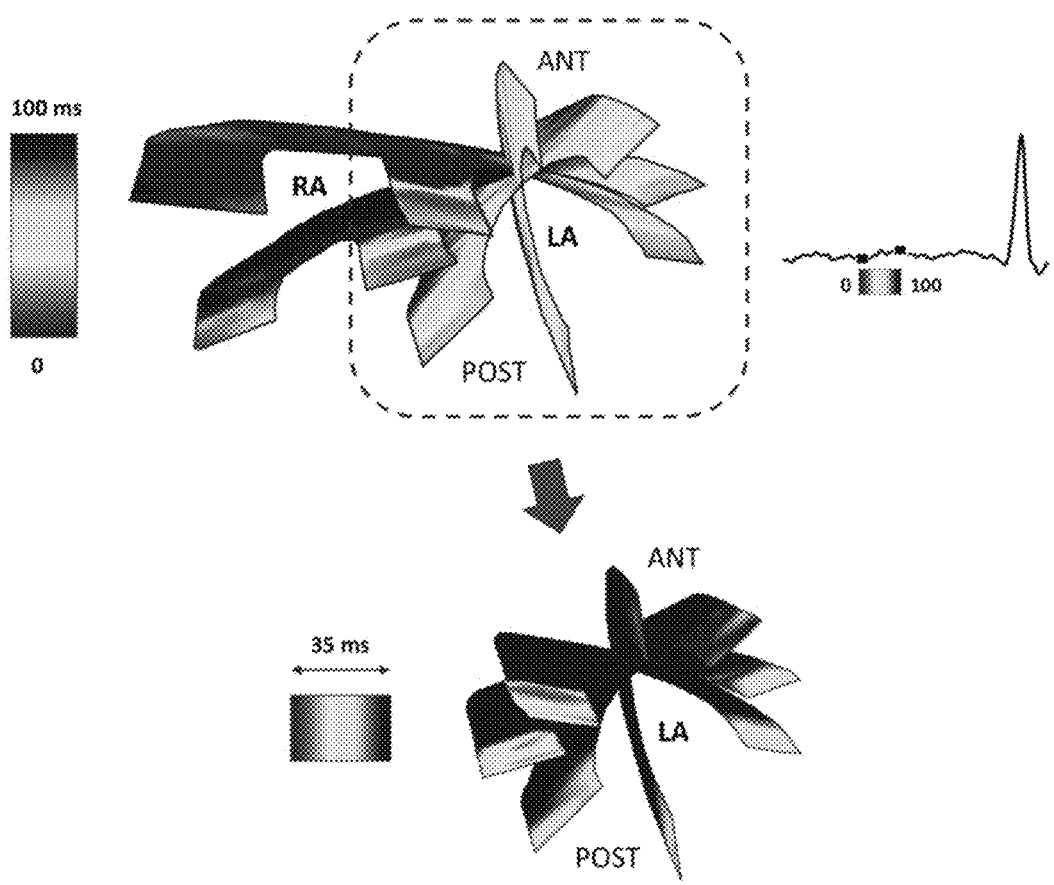
FIG. 33 is a diagram illustrating EWI isochrones of a mitral flutter displaying direction of propagation.

FIG. 33 shows the EWI isochrones of the same 61-year-old mitral flutter patient included in FIG. 25. The upper image shows the same isochrone as FIG. 25 but rotated to be viewed from an inferior perspective. Included is the 100 ms color bar and the ECG tracing. The bottom image is identical data of the left atrial isochrone, but the isochrone is displayed over a shorter time period, as seen with the 35 ms color bar. This allows for easier visualization of the direction of rotation of the flutter circuit.

EWI Compared to ECG Analysis

Six board-certified cardiac electrophysiologists were asked to predict the location of the arrhythmia by reading pre-operative 12-lead ECGs using any published algorithm they can use in clinical practice. All electrophysiologists were blinded to EWI, 3D electroanatomical maps and EPS reports. Three patients were excluded from ECG analysis due to lack of a 12-lead ECG in the appropriate rhythm (FIG. 22). ECG predictions were completed by all six electrophysiologists in the remaining 52 patients. Clinician interpretation of ECG correctly predicted 71% of the locations, with minimal inter-observer agreement by diagnosis (Kappa values: WPW=0.33; PVC=0.33, AT=0.00, AFL=0.37). EWI was more accurate than 12-lead ECG for localization of arrhythmia or pathway origins in all patients (unadjusted for arrhythmia type: OR: 11.8; 95% CI: 2.2-63.2; p=0.004; adjusted for arrhythmia type: OR: 12.1; 95% CI: 2.3-63.2; p=0.003).

Figure 26A:
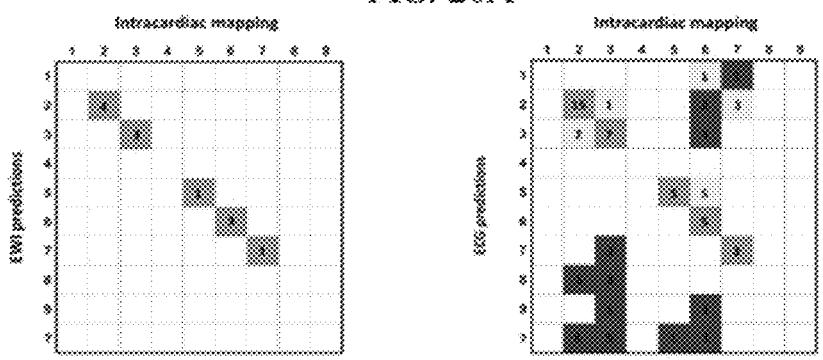
FIGS. 26A-B are example heat maps of EWI and ECG predictions vs. catheter determined locations for AP and PVC localization.
Figure 26B:
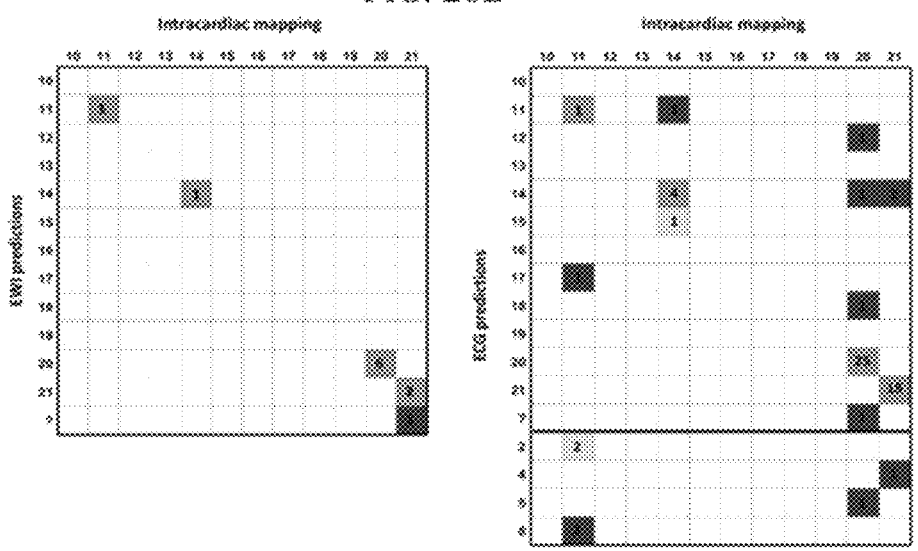

Accuracy by diagnosis, inter-observer agreement of ECG reads, and comparison of EWI with ECG are shown in table 5. Heat maps demonstrating predicted locations of the ventricular arrhythmias by EWI and cardiac electrophysiologists vs. true localization with intracardiac mapping are shown in FIG. 26. There was no change in accuracy for EWI when adjacent segments were disregarded. ECG accuracy for AP localization fell from 64% to 47% while PVC localization fell from 80% to 75% if only exact segments were considered correct. FIG. 26 shows four heat maps illustrating the EWI and ECG predictions for both (26A) WPW and (26B) PVC locations as compared to intracardiac mapping. Rows indicate EWI or ECG predictions while columns represent intracardiac mapping locations. The numbers on each axis correspond to the location as labeled in FIG. 28. The number in each cell indicates the number of predictions in that location as predicted by EWI or ECG respectively. Green indicates an exactly correct prediction. Yellow indicates a prediction in an adjacent segment, which was counted correct in the results and as displayed in Table 5. Red indicates an incorrect prediction. There was no change in accuracy for EWI if only exact predictions were considered correct. ECG accuracy for AP localization fell from 64% to 47% while PVC localization fell from 80% to 75% if only exact segments were considered correct.

Complications

There were no complications reported due to EWI within 30 days of the procedures. There were no procedural delays due to EWI scanning, which lasted 15 minutes on average.

Discussion

The disclosed technique can provide the improved clinical accuracy of multi-2D or 3D-rendered transthoracic EWI for non-invasive localization of arrhythmias in all four cardiac chambers, including WPW, PVC, AT and AFL. This was performed in an adult patient population with pre-existing cardiac disease including previous catheter ablations and/or significant other co-morbidities. The accuracy of EWI was higher than that of clinical diagnosis by electrophysiologists reading standard 12-lead ECG. When used in conjunction with standard 12-lead ECG, EWI can be a tool for diagnosis, clinical decision making, and treatment planning of patients with arrhythmias.

EWI performed in an adult population shows a consistently high rate of EWI accuracy for localizing WPW, PVC, AT and AFL in a clinically diverse and heterogeneous patient population with significant co-morbidities (Tables 3 and 4). Notably, on the prior echocardiogram, 37.5% (n=15) of patients had dilated left atria, 18% (n=7) of patients had prior evidence of wall motion abnormality, 42.5% (n=17) of patients had a decreased left ventricular ejection fraction, 20% (n=8) of patients had a previously technically limited echocardiogram and 13% (n=7) patients had previous catheter ablation procedures. These pre-existing conditions and wall motion abnormalities did not diminish EWI localization accuracy. In this cohort, EWI was shown to successfully locate the site of interest in 96% (n=53) of the 55 patients and was more accurate than 12-lead ECG (Table 5). EWI can also characterize macro-reentrant circuits in addition to focal arrhythmias (FIG. 33)

The anatomic information provided by ECGs can be limited. ECG diagnosis and localization of arrhythmias can have a high degree of inter-observer variability (Table 5). The average accuracy of 12-lead ECG localization can affect its comparison to EWI. This can be due to the usage of the standardized segmented map, which can diminish the accuracy of localization, especially since some segments were close in proximity (FIG. 26). However, given the high degree of accuracy of EWI, EWI used in conjunction with the 12-lead ECG can provide increased accuracy in the diagnosis of arrhythmias.

Figure 24A:
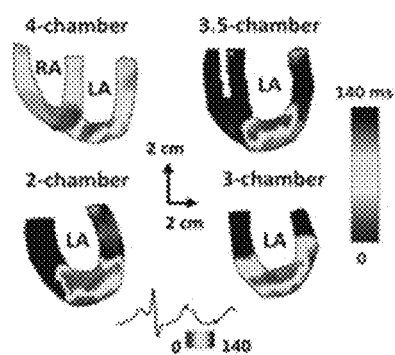
FIGS. 24A-D are example EWI isochrones of a left atrial roof tachycardia.
Figure 24B:
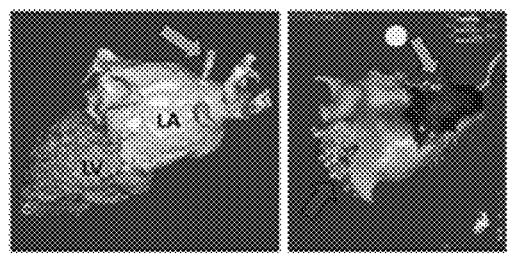
Figure 24C:
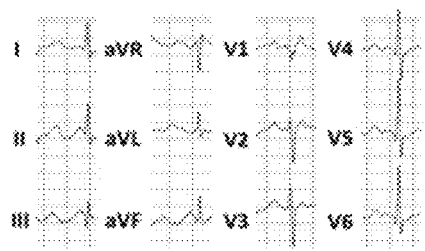
Figure 24D:
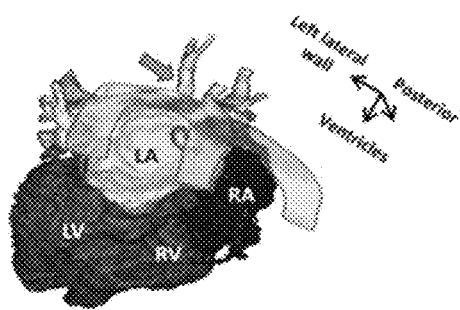

An advantage of EWI is the ease with which isochrones can demarcate the earliest sites of interest along with direct anatomic visualization similar to standard transthoracic echocardiography. For example, 12-lead ECG can be limited in diagnosing arrhythmias from the posterior side of the heart, but EWI imaging can provide 3D-rendered anatomical information. EWI isochrones can also be imported and overlaid onto 3D electroanatomic mapping systems used in the electrophysiology lab (FIG. 24D). While sites of catheter treatment can be confirmed with intracardiac catheter mapping prior to ablation, an overlay of EWI isochrones on personalized patient anatomy in 3D electroanatomic mapping systems can reduce procedural time by directing the treating electrophysiologist to the area of interest expeditiously. For example, prior knowledge of the location of origin of the focal AT, at the juncture of the accessory pulmonary vein in FIG. 24D can prevent prolonged procedure and anesthesia times and decreased radiation exposure to the patient who had previous pulmonary vein isolation. EWI can also be used immediately after unsuccessful ablation attempts, such as in FIG. 24D, to help determine the reason for failure or changes to the arrhythmia after application of ablation lesions.

Another advantage of EWI can be its use of pre-established infrastructure, using hardware that already exists in most echocardiography machines readily available in clinics and hospitals. It, therefore, can be cost-effective with a similar profile to standard 2D transthoracic echocardiography and be more cost-effective than CT or MRI. Real-time EWI can be integrated into existing standard clinical ultrasound imaging systems since no additional hardware is required. The disclosed technique can process generation of the 3D-rendered isochrones in less than 10 minutes and is currently undergoing optimization and investigation.

Certain techniques, such as ECGI, can be cost- and time-inefficient, and expose the patient to ionizing radiation since CT is required for anatomical information. These drawbacks can limit the use of ECGI as a test for the average patient presenting for evaluation of arrhythmia. In addition, unlike other imaging modalities which require in-depth user training and experience for interpretation, the isochrones generated by EWI can provide information in a clear and easy to interpret manner for a general audience. This can allow EWI a useful non-invasive tool that can be easily applied in everyday clinical practice and can be used to facilitate shared decision making between the operating electrophysiologist and patient prior to catheter ablation.

Catheter ablations can induce certain risks. For instance, trans-septal puncture has the risk of stroke and bleeding, ablation of accessory pathways near the AV node can cause heart block, and increased fluoroscopy times can carry complications from radiation exposure. EWI can provide clear anatomic localization of the site of origin of arrhythmias that can be used for pre-procedure planning. EWI used as a clinical imaging modality can improve discussion with patients about potential treatment options and planning while reducing these procedural risks and time.

FIG. 27 shows an example EWI processing on a 26-year-old healthy volunteer. 2D apical views were acquired with a diverging ultrasound sequence at a high frame rate (2000 frames/second). Axial displacements and strains are estimated on the radiofrequency data and the myocardium was segmented manually on the B-mode. The resulting four 2D electromechanical activation maps are then co-registered around the left ventricle median axis (longitudinal apex to the base rotation axis of the probe, displayed with the dotted black line) and by interpolating the multi-2D isochrones around the circumference, the 3D-rendered isochrones are generated.

Figure 35B:
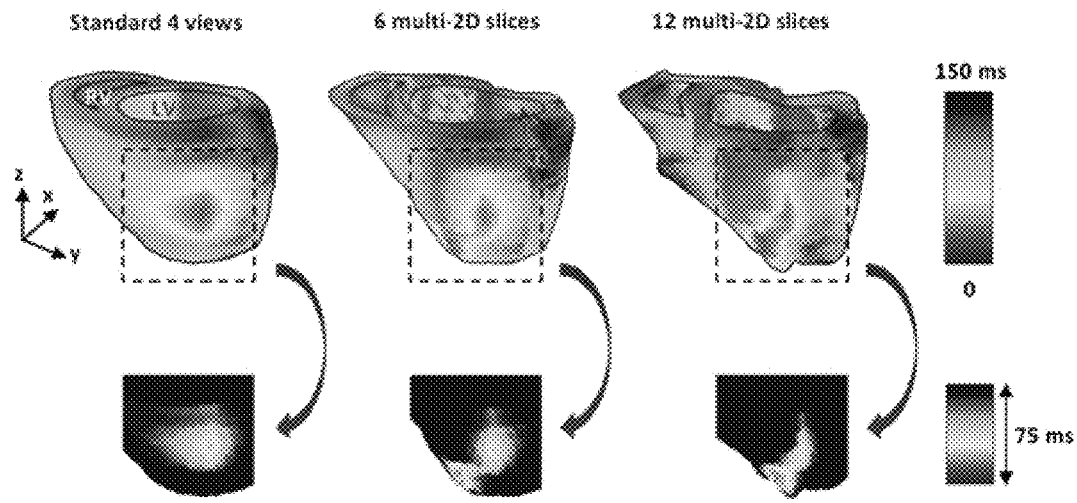

The impact of multi-2D sampling on the spatial resolution of 3D-rendered EWI was evaluated to determine the image results if the arrhythmia focus was located between two of the four standard apical slices. The results of the two open-chest canine resolution tests (FIG. 34 and FIG. 35) demonstrate that the more multi-2D slices there are sampling the circumference of interest, the earliest activated region after interpolation becomes more focal and the distance computed from the 3D-rendered isochrones between the pacing electrodes are closer to the true values measured on the surface of the heart (FIGS. 34A and 34B). The 12 multi-2D slices (FIG. 35B) in comparison to the 4 and 6 multi-2D slices, displays early activation with the most distinct focus. Even in the standard 3D-rendered isochrones generated with 4 multi-2D slices, EWI localized the pacing locations, albeit in a less precise and wider region displayed in orange due to the effect of the interpolation on a broader circumference (FIG. 34C and FIG. 35B). Increasing the number of multi-2D slices acquired can improve imaging spatial resolution for arrhythmia localization. This can also prolong EWI scan durations.

FIG. 34 shows the results of a 3D-rendered EWI spatial resolution test on a 29.6 kg open-chest male canine with five different LV pacing locations. For all isochrones, red represents the earliest activated region and blue the latest. FIG. 34A shows a picture of the canine's LV with sutures marking the pacing locations (top) and schematic of the distances between the pacing electrodes as measured on the epicardium surface of the LV (bottom). FIG. 34B shows a table listing the 3D coordinates of the earliest activated voxel in each of the five 3D-rendered isochrones (top) and a table showing the distances between the LV pacing electrodes (d12, d23, etc.) as computed from the 3D-rendered isochrone earliest activated voxels compared to the true measurements (bottom). FIG. 34C shows 3D-rendered isochrones of the ventricles in anterior view for each of the five LV pacing locations.

FIG. 35 shows the results of a 3D-rendered EWI multi-2D sampling resolution on a 28 kg open-chest male canine with a single LV pacing location. For all isochrones red represents the earliest activated region and blue the latest. FIG. 35A shows a schematic of the multi-2D sampling slice locations around the circumference of the canine's ventricles. The thick black lines represent the slice positions of the usual four acquired apical multi-2D views, while the thin lines and the dashed lines represent the locations of the additional views for a total of 6 and 12 evenly spaced slices respectively. The pacing electrode falls between two of the four standard views (3- and 2-chamber), but lies on one of the additional EWI views considered for both 6 and 12 multi-2D slices 3D-rendered isochrones. FIG. 35B shows 3D-rendered isochrones of the ventricles in anterior view generated with (from left to right) the standard 4 apical views, 6 apical slices evenly spaced by 30 degree and 12 apical slices evenly spaced by 15 degree (top) and a portion (within the dashed square) of the same 3D-rendered isochrones displayed with a shorter colorbar scale (75 ms) to better contrast the focal spot (bottom).

EWI with 3D ultrasound can allow visualization of the entire myocardial volume in a single heartbeat and increase the accuracy of EWI. Temporal co-registration of the four multi-2D isochrone views can rely on manual p-wave or QRS origin selection on a single lead ECG, which corresponds to the earliest possible activation (0 ms). Heart rhythm and ECG morphology were the same across all four views for each beat processed before combining the multi-2D views. Repeating the origin selection process to have consistent isochrone starting times across the views can be performed, for example, for AFLs. The activation time origin was systematically picked on each view's ECG by measuring a constant interval from the immediate R wave or p-wave peak. Utilizing high volume-rate 3D EWI can avoid errors induced by multi-2D view co-registration, as well as out of plane motion, since whole heart cardiac electromechanical activity can be mapped in a single heartbeat.

The disclosed techniques can provide 3D EWI in open-chest canines in sinus rhythm, left ventricular pacing and ventricular tachycardia. A 3D EWI with a 32×32 matrix array was used in a clinical setting on a healthy volunteer in sinus rhythm and in a cardiac resynchronization therapy patient during both right ventricular pacing only, and biventricular pacing.

The contents of all figures and all references, patents and published patent applications and Accession numbers cited throughout this application are expressly incorporated herein by reference.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalent.

What is claimed is:

1. A method for generating an electromechanical map corresponding to a location of a heart from ultrasound data generated using an ultrasound beam, comprising:
    obtaining ultrasound data including a series of image frames and radio frequency (RF) signals corresponding to the location;
    measuring displacements and strains based on the ultrasound data to determine an electromechanical activation in the location;
    converting the ultrasound data into a series of isochrone maps, wherein the series of isochrone maps illustrates the electromechanical activation, wherein the series of isochrone maps comprises at least four isochrone maps;
    determining a median axis of each of the isochrone maps;
    determining a location of an internal wall structure of the heart and a value of the electromechanical activation at the location of the internal wall structure at a point of the median axis in the isochrone maps, wherein the values of the electromechanical activation are determined from at least eight locations of the internal wall structure; and
    generating the electromechanical map by combining the locations and the value of the electromechanical activation wherein the electromechanical map is a three-dimensional (3D) map configured to illustrate the internal wall structure of the heart at the location.

2. The method of claim 1, wherein the ultrasound data corresponds to multiple apical views of the location.

3. The method of claim 1, wherein the determining the electromechanical activation further includes beamforming the RF signals.

4. The method of claim 1, wherein the determining the electromechanical activation comprises identifying zero-crossings of the strains at the location of the heart.

5. The method of claim 4, wherein the converting the ultrasound data into the series of isochrone maps further comprises interpolating the zero-crossings into the series of isochrone maps to show the electromechanical activation over time.

6. The method of claim 1, further comprising obtaining an electrocardiography (ECG) signal to align the series of image frames and RF signals.

7. The method of claim 1, wherein the ultrasound data is obtained over a duration of one or more cardiac cycles.

8. The method of claim 1, wherein the electromechanical map illustrates the electromechanical activation, the displacements, and the strains over a duration of one or more cardiac cycles.

9. The method of claim 1, further comprising obtaining a segmented image of the heart from the series of image frames.

10. The method of claim 1, further comprising performing a linear interpolation between the at least eight locations.

11. A system for generating an electromechanical map corresponding to a location of a heart from ultrasound data generated using an ultrasound beam, comprising:
    at least one ultrasound system, configured to obtain ultrasound data comprising a series of image frames and radio frequency (RF) signals corresponding to the location; and
    a processor, coupled to the system, and configured to
        measure displacements and strains based on the ultrasound data to determine an electromechanical activation in the location;

convert the ultrasound data into a series of isochrone maps, wherein the series of isochrone maps comprises at least four isochrone maps;

determine a median axis of each of the isochrone maps;

determine a location of an internal wall structure of the heart and a value of the electromechanical activation at the location of the internal wall structure at a point of the median axis in the isochrone maps, wherein the values of the electromechanical activation are determined from at least eight locations of the internal wall structure; and generate the electromechanical map by combining the locations and the value of the electromechanical activation, wherein the electromechanical map is a three-dimensional (3D) map configured to illustrate the internal wall structures of the heart at the location.

12. The system of claim 11, wherein the processor is further configured to identify zero-crossings of the strains at the location of the heart based on the ultrasound data.

13. The system of claim 11, wherein the at least one ultrasound system comprises a 2D array including a plurality of transducer elements.

14. The system of claim 11, wherein the at least one ultrasound system is configured to perform a diverging imaging sequence and/or a focused wave imaging sequence.

15. The system of claim 11, wherein the processor is further configured to generate a heart model for an electromechanical simulation and an ultrasound simulation based on the series of image frames and radio frequency (RF) signals corresponding to the location in the heart.

16. The system of claim 11, wherein the processor is further configured to obtain a segmented image of the heart from the series of image frames.

17. The system of claim 11, the processor is configured to perform a linear interpolation between the at least eight locations.

\* \* \* \* \*

UNITED STATES PATENT AND TRADEMARK OFFICE
CERTIFICATE OF CORRECTION

| | |
|---|---|
| PATENT NO. | : 11,678,859 B2 |
| APPLICATION NO. | : 16/572328 |
| DATED | : June 20, 2023 |
| INVENTOR(S) | : Elisa Konofagou et al. |

It is certified that error appears in the above-identified patent and that said Letters Patent is hereby corrected as shown below:

In the Specification

Column 1, Lines 19-23, delete paragraph and replace with the following:
--This invention was made with government support under HL114358, and EB006042 awarded by the National Institutes of Health. The government has certain rights in the invention.--

Signed and Sealed this
Seventeenth Day of October, 2023

Katherine Kelly Vidal
*Director of the United States Patent and Trademark Office*